United States Patent
Ida et al.

(10) Patent No.: US 10,426,712 B2
(45) Date of Patent: Oct. 1, 2019

(54) DENTAL POLYMERIZABLE COMPOSITION

(71) Applicant: KURARAY NORITAKE DENTAL INC., Kurashiki-shi (JP)

(72) Inventors: Hirotsugu Ida, Tsukuba (JP); Kenji Suzuki, Tainai (JP); Seiya Shimizu, Moriya (JP); Kenji Shachi, Tsukuba (JP); Kazuhiko Maekawa, Kurashiki (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 34 days.

(21) Appl. No.: 15/511,276

(22) PCT Filed: Sep. 16, 2015

(86) PCT No.: PCT/JP2015/004741
§ 371 (c)(1),
(2) Date: Mar. 15, 2017

(87) PCT Pub. No.: WO2016/042770
PCT Pub. Date: Mar. 24, 2016

(65) Prior Publication Data
US 2017/0290746 A1 Oct. 12, 2017

(30) Foreign Application Priority Data

Sep. 17, 2014 (JP) ................. 2014-189181

(51) Int. Cl.
| A61K 6/083 | (2006.01) |
| A61K 6/00 | (2006.01) |
| C08F 4/54 | (2006.01) |
| C08F 297/02 | (2006.01) |

(52) U.S. Cl.
CPC ............ *A61K 6/083* (2013.01); *A61K 6/00* (2013.01); *A61K 6/005* (2013.01); *A61K 6/0023* (2013.01); *A61K 6/0052* (2013.01); *A61K 6/0088* (2013.01); *A61K 6/0091* (2013.01); *C08F 4/54* (2013.01); *C08F 297/026* (2013.01)

(58) Field of Classification Search
None
See application file for complete search history.

(56) References Cited

U.S. PATENT DOCUMENTS

| 5,264,527 | A | 11/1993 | Varshney et al. |
| 6,329,480 | B1* | 12/2001 | Uchiumi ............ C08F 20/12 526/173 |
| 6,395,259 | B1 | 5/2002 | Shalaby |
| 2002/0187113 | A1 | 12/2002 | Shalaby |
| 2004/0162375 | A1 | 8/2004 | Ali et al. |
| 2005/0234199 | A1 | 10/2005 | Taniguchi et al. |
| 2006/0142511 | A1 | 6/2006 | Couturier et al. |
| 2006/0167199 | A1 | 7/2006 | Yamago et al. |
| 2009/0118383 | A1* | 5/2009 | Mori .......................... C08F 8/30 521/38 |
| 2011/0027195 | A1* | 2/2011 | Maurat ................ A61K 6/0011 424/54 |
| 2012/0196952 | A1* | 8/2012 | Suzuki ................ A61K 6/0023 523/116 |
| 2012/0238662 | A1* | 9/2012 | Klee .................... A61K 6/0038 523/116 |
| 2013/0289216 | A1* | 10/2013 | Klee .................... A61K 6/0835 525/285 |
| 2015/0038658 | A1* | 2/2015 | Tanabe ...................... C08F 4/56 526/177 |

FOREIGN PATENT DOCUMENTS

| DE | 2802360 A1 * | 7/1978 | ............ C08F 277/00 |
| JP | 5-507737 A | 11/1993 | |
| JP | 6-93060 A | 4/1994 | |
| JP | 11-335432 | 12/1999 | |

(Continued)

OTHER PUBLICATIONS

Extended Search Report dated Apr. 30, 2018 in European Patent Application No. 15842045.5.

(Continued)

*Primary Examiner* — Peter A Salamon
(74) *Attorney, Agent, or Firm* — Oblon, McClelland, Maier & Neustadt, L.L.P.

(57) ABSTRACT

The present invention provides a dental polymerizable composition that requires less discharging force, is easily formable, has low polymerization shrinkage stress during curing, and exhibits high stain resistance and surface gloss when cured. The present invention relates to a dental polymerizable composition including a (meth)acrylic block copolymer (A), a polymerizable monomer (B), and a polymerization initiator (C). The (meth)acrylic block copolymer (A) consists of a (meth)acrylic polymer block (a) having a curable functional group and a (meth)acrylic polymer block (b) having no curable functional group. The curable functional group has a partial structure represented by the following general formula (1):

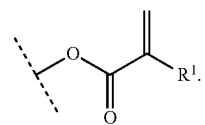

(1)

16 Claims, No Drawings

(56) References Cited

FOREIGN PATENT DOCUMENTS

| | | |
|---|---|---|
| JP | 3040172 B2 | 5/2000 |
| JP | 2000-159621 A | 6/2000 |
| JP | 2000-212218 A | 8/2000 |
| JP | 3639859 B2 | 4/2005 |
| JP | 2006-523726 A | 10/2006 |
| JP | 3839829 B2 | 11/2006 |
| JP | 2008-201892 A | 9/2008 |
| JP | 2011-184678 A | 9/2011 |
| JP | 2013-513630 A | 4/2013 |
| JP | 2014-501821 A | 1/2014 |
| WO | 96/30421 A1 | 10/1996 |
| WO | 98/01478 A1 | 1/1998 |
| WO | 2004/013192 A1 | 2/2004 |
| WO | 2004/014926 A2 | 2/2004 |
| WO | 2004/069886 A1 | 8/2004 |
| WO | 2011/048802 A1 | 4/2011 |
| WO | 2011/072812 A1 | 6/2011 |
| WO | 2012/084206 A1 | 6/2012 |
| WO | 2013/141105 A1 | 9/2013 |

OTHER PUBLICATIONS

International Search Report dated Dec. 15, 2015, in PCT/JP2015/004741, filed Sep. 16, 2015.

* cited by examiner

DENTAL POLYMERIZABLE COMPOSITION

TECHNICAL FIELD

The present invention relates to a dental polymerizable composition.

BACKGROUND ART

Adhesive materials or filling materials are used for restorative treatment of teeth, bones, etc. Dental polymerizable compositions containing a polymerizable monomer, a polymerization initiator, a filler, etc., are generally used as such adhesive materials or filling materials. A dental polymerizable composition is used in the form of a cured product obtained by polymerizing a polymerizable monomer in the composition having been formed into a desired shape. Specifically, such dental polymerizable compositions are used in applications such as mobile tooth fixing materials, denture liners, dental cements, and dental self-adhesive composite resins. A mobile tooth fixing material is a material for fixing a loose tooth (mobile tooth) to the adjacent healthy teeth. A denture liner is a material for improving the adaptation of a denture used. A dental cement is a material used to bond a prosthesis (such as an inlay, a crown, a bridge, a denture, or an implant) to a missing portion of a tooth. When it is checked whether such a prosthesis functions properly in an oral cavity for a certain period of time, a temporary dental cement is used so that the prosthesis can be removed from a missing portion after the check. A dental self-adhesive composite resin is a material for filling a missing portion of a tooth.

A dental polymerizable composition must be easily formed into a desired shape when applied directly from a container. Specifically, the composition must be capable of being discharged from the container with less discharging force and being formed into a desired shape immediately after being discharged. On the other hand, a cured product obtained from the dental polymerizable composition thus formed is required to have surface gloss, stain resistance, etc.

A mobile tooth fixing material as a cured product is required to have shock absorbing capacity and adhesion to enamel when subjected to an external force. The cured product must have a flexural modulus within an appropriate range to increase its shock absorbing capacity. A denture liner as a cured product is required to have low surface hardness and high distortion resistance. A dental cement, particularly a temporary dental cement, as cured product, is required to have a flexural modulus within an appropriate range so that it can be removed. In terms of close adhesion to a missing portion of a tooth, a dental self-adhesive composite resin is required to reduce polymerization shrinkage stress during curing.

As dental polymerizable compositions that meet these requirements, those containing an elastomer have been known. For example, Patent Literature 1 has reported a dental polymerizable composition containing an acrylic block copolymer consisting of a polymethacrylic acid ester and a polyacrylic acid ester. There is, however, a demand for further improved dental polymerizable compositions that require less discharging force, reduce polymerization shrinkage stress during curing, and form a cured product having higher resistance to stain, distortion, etc.

CITATION LIST

Patent Literature

Patent Literature 1: WO 2011/048802 A1

SUMMARY OF INVENTION

Technical Problem

It is therefore an object of the present invention to provide a dental polymerizable composition that requires less discharging force, is easily formable, has low polymerization shrinkage stress during curing, and exhibits high stain resistance and surface gloss when cured. It is another object of the present invention to provide a mobile tooth fixing material that requires less discharging force, is easily formable, has low polymerization shrinkage stress during curing, and exhibits high stain resistance, shock absorbing capacity, surface gloss, and adhesion to enamel when cured. It is still another object of the present invention to provide a denture liner that requires less discharging force, is easily formable, has low polymerization shrinkage stress during curing, and exhibits high stain resistance, flexibility, distortion resistance, and surface gloss when cured. It is still another object of the present invention to provide a dental cement that requires less discharging force, is easily formable, has low polymerization shrinkage stress during curing, and exhibits high stain resistance, shock absorbing capacity, and surface gloss when cured. It is yet still another object of the present invention to provide a dental self-adhesive composite resin that requires less discharging force, is easily formable, has low polymerization shrinkage stress during curing, and further exhibits high stain resistance, surface gloss, and adhesion to tooth structure (enamel and dentin).

Solution to Problem

According to the present invention, the above-mentioned objects can be achieved by providing:

[1] a dental polymerizable composition including:
a (meth)acrylic block copolymer (A) consisting of a (meth)acrylic polymer block (a) having a curable functional group (hereinafter simply referred to as a "(meth)acrylic polymer block (a)") and a (meth)acrylic polymer block (b) having no curable functional group (hereinafter simply referred to as a "(meth)acrylic polymer block (b)"), the curable functional group having a partial structure represented by the following general formula (1) (hereinafter referred to as a "partial structure (1)"):

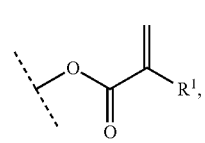

(1)

where $R^1$ represents a hydrogen atom or a hydrocarbon group having 1 to 20 carbon atoms;
a polymerizable monomer (B); and
a polymerization initiator (C);

[2] the dental polymerizable composition according to [1], wherein the curable functional group having the partial structure represented by the general formula (1) is a curable functional group represented by the following general formula (2):

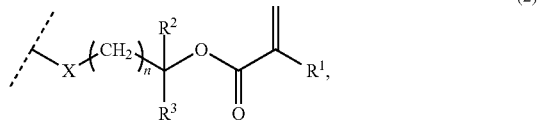

(2)

where $R^1$ represents a hydrogen atom or a hydrocarbon group having 1 to 20 carbon atoms, $R^2$ and $R^3$ each independently represent a hydrogen atom or a hydrocarbon group having 1 to 6 carbon atoms, X represents O, S, or $N(R^6)$ (where $R^6$ represents a hydrogen atom or a hydrocarbon group having 1 to 6 carbon atoms), and n represents an integer of 1 to 20;
[3] the dental polymerizable composition according to [2], wherein in the general formula (2), $R^1$ represents a hydrogen atom or a methyl group, and X is O;
[4] the dental polymerizable composition according to any one of [1] to [3], further including a polymerization accelerator (D);
[5] the dental polymerizable composition according to any one of [1] to [4], further including a filler (E);
[6] a mobile tooth fixing material including the dental polymerizable composition according to any one of [1] to [5];
[7] a denture liner including the dental polymerizable composition according to any one of [1] to [5];
[8] a dental cement including the dental polymerizable composition according to any one of [1] to [5]; and
[9] a dental self-adhesive composite resin including the dental polymerizable composition according to any one of [1] to [5].

Advantageous Effects of Invention

The dental polymerizable composition of the present invention requires less discharging force, is easily formable, has low polymerization shrinkage stress during curing, and exhibits high stain resistance and surface gloss when cured. The mobile tooth fixing material of the present invention requires less discharging force, is easily formable, has low polymerization shrinkage stress during curing, and exhibits high stain resistance, shock absorbing capacity, surface gloss, and adhesion to enamel when cured. The denture liner of the present invention requires less discharging force, is easily formable, has low polymerization shrinkage stress during curing, and exhibits high flexibility, distortion resistance, stain resistance, and surface gloss when cured. The dental cement of the present invention requires less discharging force, is easily formable, has low polymerization shrinkage stress during curing, and exhibits high stain resistance, shock absorbing capacity, and surface gloss when cured. The dental self-adhesive composite resin of the present invention requires less discharging force, is easily formable, has low polymerization shrinkage stress during curing, and further exhibits high stain resistance, surface gloss, and adhesion to tooth structure (enamel and dentin) when cured.

DESCRIPTION OF EMBODIMENTS

Hereinafter, the present invention will be described in detail. The dental polymerizable composition of the present invention includes a (meth)acrylic block copolymer (A). As used herein, the term "(meth)acrylic" refers to either "acrylic" or "methacrylic. The term "(meth)acryloyl" described later refers to either "acryloyl" or "methacryloyl". The term "(meth)acrylate" described later refers to either "acrylate" or "methacrylate".

In terms of flexibility and discharging force, the content of the (meth)acrylic block copolymer (A) in the dental polymerizable composition of the present invention is preferably 0.5 to 90 mass %, more preferably 5 to 80 mass %, and even more preferably 10 to 80 mass %.

When the dental polymerizable composition of the present invention is used as a mobile tooth fixing material for treatment of mobile teeth, the content of the (meth)acrylic block copolymer (A) in the dental polymerizable composition is preferably 2 to 80 mass %, more preferably 5 to 70 mass %, and even more preferably 10 to 70 mass %.

When the dental polymerizable composition of the present invention is used as a denture liner for dental treatment, the content of the (meth)acrylic block copolymer (A) in the dental polymerizable composition is preferably 3 to 90 mass %, more preferably 10 to 80 mass %, and even more preferably 45 to 80 mass %.

When the dental polymerizable composition of the present invention is used as a cement for dental treatment, the content of the (meth)acrylic block copolymer (A) in the dental polymerizable composition is preferably 0.5 to 80 mass %, more preferably 1 to 60 mass %, and even more preferably 5 to 50 mass %. When such a dental cement is used for temporary cementation in dental treatment, the content of the (meth)acrylic block copolymer (A) in the dental polymerizable composition is preferably 5 to 80 mass %, more preferably 10 to 70 mass %, and even more preferably 10 to 55 mass %.

When the dental polymerizable composition of the present invention is used as a self-adhesive composite resin for dental treatment, the content of the (meth)acrylic block copolymer (A) in the dental polymerizable composition is preferably 1 to 65 mass %, more preferably 2 to 40 mass %, and even more preferably 3 to 35 mass %.

The (meth)acrylic block copolymer (A) includes (meth)acrylic polymer block (a). The (meth)acrylic polymer block (a) has a curable functional group having a partial structure (1).

The partial structure (1) is represented by the following general formula (1)

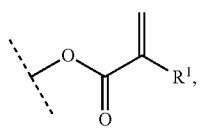

(1)

where $R^1$ represents a hydrogen atom or a hydrocarbon group having 1 to 20 carbon atoms.

Examples of the hydrocarbon group having 1 to 20 carbon atoms and represented by $R^1$ in the above general formula (1) include: alkyl groups such as methyl, ethyl, n-propyl, isopropyl, n-butyl, isobutyl, sec-butyl, t-butyl, 2-methylbutyl, 3-methylbutyl, 2-ethylbutyl, 3-ethylbutyl, 2,2-dimethylbutyl, 2,3-dimethylbutyl, n-pentyl, neopentyl, n-hexyl, 2-methylpentyl, 3-methylpentyl, and n-decyl groups; cycloalkyl groups such as cyclopropyl, cyclobutyl, cyclopentyl, and cyclohexyl groups; aryl groups such as phenyl and naphthyl groups; and aralkyl groups such as benzyl and phenylethyl groups. In terms of the cure rate, particularly preferred are methyl and ethyl groups, and most preferred is a methyl group.

In terms of increasing the cure rate of the dental polymerizable composition of the present invention, the curable functional group having the partial structure (1) of the (meth)acrylic polymer block (a) in the (meth)acrylic block copolymer (A) is preferably represented by the following general formula (2) (hereinafter, the curable "curable functional group (2)":

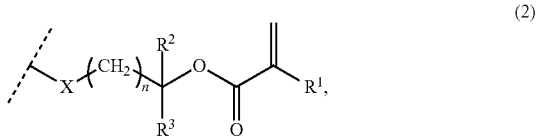

(2)

where $R^1$ represents a hydrogen atom or a hydrocarbon group having 1 to 20 carbon atoms, $R^2$ and $R^3$ each independently represent a hydrogen atom or a hydrocarbon group having 1 to 6 carbon atoms, X represents O, S, or $N(R^6)$ (where $R^6$ represents a hydrogen atom or a hydrocarbon group having 1 to 6 carbon atoms), and n represents an integer of 1 to 20.

Specific examples and preferred examples of the hydrocarbon group having 1 to 20 carbon atoms and represented by $R^1$ in the general formula (2) are the same as those listed as examples of the hydrocarbon group represented by $R^1$ in the above general formula (1).

In the above general formula (2), $R^2$ and $R^3$ each independently represent a hydrogen atom or a hydrocarbon group having 1 to 6 carbon atoms, and $R^2$ and $R^3$ are each preferably a hydrocarbon group having 1 to 6 carbon atoms because such a hydrocarbon group can be easily and directly introduced using a monomer containing a di(meth)acrylate (3) described later. Examples of such a hydrocarbon group include: alkyl groups such as methyl, ethyl, n-propyl, isopropyl, n-butyl, isobutyl, sec-butyl, t-butyl, 2-methylbutyl, 3-methylbutyl, 2-ethylbutyl, 3-ethylbutyl, 2,2-dimethylbutyl, 2,3-dimethylbutyl, n-pentyl, neopentyl, n-hexyl, 2-methylpentyl, and 3-methylpentyl groups; cycloalkyl groups such as cyclopropyl, cyclobutyl, cyclopentyl, and cyclohexyl groups; and aryl groups such as a phenyl group. Particularly preferred are methyl and ethyl groups, and most preferred is a methyl group, in terms of the cure rate of the dental polymerizable composition of the present invention.

In the above general formula (2), X represents O, S, or $N(R^6)$ ($R^6$ represents a hydrogen atom or a hydrocarbon group having 1 to 6 carbon atoms), and X is preferably O because of ease of polymerization control. When X is $N(R^6)$, examples of the hydrocarbon group having 1 to 6 carbon atoms and represented by $R^6$ include: alkyl groups such as methyl, ethyl, n-propyl, isopropyl, n-butyl, isobutyl, sec-butyl, t-butyl, 2-methylbutyl, 3-methylbutyl, 2-ethylbutyl, 3-ethylbutyl, 2,2-dimethylbutyl, 2,3-dimethylbutyl, n-pentyl, neopentyl, n-hexyl, 2-methylpentyl, and 3-methylpentyl groups; cycloalkyl groups such as cyclopropyl, cyclobutyl, cyclopentyl, and cyclohexyl groups; and a phenyl group.

In the above general formula (2), the integer of 1 to 20 represented by n is preferably 2 to 5 in terms of increasing the cure rate of the dental polymerizable composition of the present invention. In the general formula (2), X is selected from the group consisting of O, S, and $N(R^5)$ ($R^5$ is a hydrogen atom or a hydrocarbon group having 1 to 6 carbon atoms), and X is preferably O because of ease of polymerization control. When X is $N(R^5)$, examples of the hydrocarbon group having 1 to 6 carbon atoms and represented by $R^5$ include: alkyl groups such as methyl, ethyl, n-propyl, isopropyl, n-butyl, isobutyl, sec-butyl, t-butyl, 2-methylbutyl, 3-methylbutyl, 2-ethylbutyl, 3-ethylbutyl, 2,2-dimethylbutyl, 2,3-dimethylbutyl, n-pentyl, neopentyl, n-hexyl, 2-methylpentyl, and 3-methylpentyl groups; cycloalkyl groups such as cyclopropyl, cyclobutyl, cyclopentyl, and cyclohexyl groups; and a phenyl group.

The content of the partial structure (1) is preferably in the range of 0.2 to 100 mol %, more preferably in the range of 10 to 90 mol %, and even more preferably in the range of 25 to 80 mol % with respect to the total monomer units that form the (meth)acrylic polymer block (a).

The (meth)acrylic polymer block (a) includes a monomer unit formed by polymerizing a monomer containing a (meth)acrylic acid ester. As such a (meth)acrylic acid ester, a monofunctional (meth)acrylic acid ester having one (meth)acryloyl group or a polyfunctional (meth)acrylic acid ester having two or more (meth)acryloyl groups.

Examples of the monofunctional (meth)acrylic acid ester that may be used to form the (meth)acrylic polymer block (a) include methyl (met)acrylate, ethyl (meth)acrylate, n-propyl (meth)acrylate, isopropyl (meth)acrylate, n-butyl (meth)acrylate, t-butyl (meth)acrylate, cyclohexyl (meth)acrylate, 2-ethylhexyl (meth)acrylate, isobornyl (meth)acrylate, dodecyl (meth)acrylate, 2-methoxyethyl (meth)acrylate, 2-hydroxyethyl (meth)acrylate, 2-hydroxybutyl (meth)acrylate, 3-(trimethoxysilyl)propyl (meth)acrylate, 2-aminoethyl (meth)acrylate, 2-(N,N-dimethylamino)ethyl (meth)acrylate, 2-(N,N-diethylamino)ethyl (meth)acrylate, phenyl (meth)acrylate, naphthyl (meth)acrylate, 2-(trimethylsilyloxy)ethyl (meth)acrylate, 3-(trimethylsilyloxy)propyl (meth)acrylate, glycidyl (meth)acrylate, γ-((meth)acryloyloxypropyl)trimethoxysilane, ethylene oxide adducts of (meth)acrylic acid, trifluoromethylmethyl (meth)acrylate, 2-trifluoromethylethyl (meth)acrylate, 2-(perfluoroethyl)ethyl (meth)acrylate, 2-perfluoroethyl-2-perfluorobutylethyl (meth)acrylate, 2-perfluoroethyl (meth)acrylate, perfluoromethyl (meth)acrylate, diperfluoromethylmethyl (meth)acrylate, 2-perfluoromethyl-2-perfluoroethylmethyl (meth)acrylate, 2-(perfluorohexyl)ethyl (meth)acrylate, 2-(perfluorodecyl)ethyl (meth)acrylate, and 2-(perfluorohexadeyl)ethyl (meth)acrylate. Among these, preferred are methacrylic acid alkyl esters having an alkyl group having 5 or less carbon atoms, such as methyl methacrylate, ethyl methacrylate, n-propyl methacrylate, isopropyl methacrylate, n-butyl methacrylate, and t-butyl methacrylate, and most preferred is methyl methacrylate.

When a difunctional (meth)acrylic acid ester represented by the following general formula (3) (hereinafter referred to as a "di(meth)acrylate (3)")

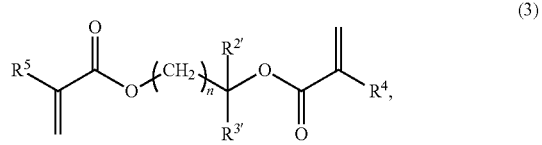

(3)

where $R^{2'}$ and $R^{3'}$ each independently represent a hydrocarbon group having 1 to 6 carbon atoms, $R^4$ and $R^5$ each independently represent a hydrogen atom or a methyl group, and n represents an integer of 1 to 20, is used as a polyfunctional (meth)acrylic acid ester that may be used to form the (meth)acrylic polymer block (a), during living anionic polymerization under the conditions described later, one of (meth)acryloyloxy groups (i.e., a (meth)acryloyloxy group represented by "CH$_2$=C(R$^5$)C(O)O" in the above general formula (3)) is selectively polymerized to form a (meth)acrylic polymer block (a) having a curable functional group (2) represented by the formula (2), where R$^1$ is R$^4$ in the formula (3), R$^2$ is R$^{2'}$ in the formula (3), R$^3$ is R$^{3'}$ in the formula (3), and X is O.

Examples of the hydrocarbon groups having 1 to 6 carbon atoms and represented by R$^{2'}$ and R$^{3'}$ in the general formula (3) are the same as those listed as examples of the hydrocarbon groups represented by R$^2$ and R$^3$ in the above general formula (2).

In terms of increasing the selectivity of polymerization, R$^4$ is preferably a methyl group. In terms of the productivity of the di(meth)acrylate (3), R$^4$ and R$^5$ are preferably the same as each other. In view of these, it is most preferable that R$^4$ and R$^5$ be both methyl groups.

Specific examples of the di(meth)acrylate (3) include 1,1-dimethylpropane-1,3-diol di(meth)acrylate, 1,1-dimethylbutane-1,4-diol di(meth)acrylate, 1,1-dimethylpentane-1,5-diol di(meth)acrylate, 1,1-dimethylhexane-1,6-diol di(meth)acrylate, 1,1-diethylpropane-1,3-diol di(meth)acrylate, 1,1-diethylbutane-1,4-diol di(meth)acrylate, 1,1-diethylpentane-1,5-diol di(meth)acrylate, and 1,1-diethylhexane-1,6-diol di(meth)acrylate. Preferred are 1,1-dimethylpropane-1,3-diol dimethacrylate, 1,1-dimethylbutane-1,4-diol dimethacrylate, 1,1-dimethylpentane-1,5-diol dimethacrylate, 1,1-dimethylhexane-1,6-diol dimethacrylate, 1,1-diethylpropane-1,3-diol dimethacrylate, 1,1-diethylbutane-1,4-diol dimethacrylate, 1,1-diethylpentane-1,5-diol dimethacrylate, and 1,1-diethylhexane-1,6-diol dimethacrylate. More preferred are 1,1-dimethylpropane-1,3-diol dimethacrylate, 1,1-dimethylbutane-1,4-diol dimethacrylate, 1,1-dimethylpentane-1,5-diol dimethacrylate, and 1,1-dimethylhexane-1,6-diol dimethacrylate.

These (meth)acrylic acid esters may be used alone or in combination with one another.

In the (meth)acrylic polymer block (a), the content of the monomer unit formed from a (meth)acrylic acid ester is preferably in the range of 90 to 100 mol %, more preferably in the range of 95 to 100 mol %, and may be 100 mol % with respect to the total monomer units that form the (meth)acrylic polymer block (a). When the (meth)acrylic polymer block (a) includes a monomer unit formed from a di(meth)acrylate (3), the content of the monomer unit formed from the di(meth)acrylate (3) is preferably in the range of 0.2 to 100 mol %, more preferably in the range of 10 to 90 mol %, and even more preferably in the range of 25 to 80 mol % with respect to the total monomer units that form the (meth)acrylic polymer block (a). Furthermore, when the (meth)acrylic polymer block (a) includes a monomer unit formed from methyl methacrylate and a monomer unit formed from a di(meth)acrylate (3), the total content of the monomer unit formed from the methyl methacrylate and the monomer unit formed from the di(meth)acrylate (3) is preferably in the range of 80 to 100 mol %, more preferably in the range of 90 to 100 mol %, even more preferably in the range of 95 to 100 mol %, and may be 100 mol % with respect to the total monomer units formed from (meth) acrylic acid esters.

The (meth)acrylic polymer block (a) may include a monomer unit formed from a monomer other than the (meth) acrylic acid esters mentioned above. Examples of such an additional monomer include: α-alkoxyacrylic acid esters such as methyl α-methoxyacrylate and methyl α-ethoxyacrylate; crotonic acid esters such as methyl crotonate and ethyl crotonate; 3-alkoxyacrylic acid esters such as 3-methoxyacrylic acid esters; (meth)acrylamides such as N-isopropyl (meth)acrylamide, N-t-butyl (meth)acrylamide, N,N-dimethyl (meth)acrylamide, and N,N-diethyl (meth) acrylamide; methyl 2-phenylacrylate; ethyl 2-phenylacrylate; n-butyl 2-bromoacrylate; methyl 2-bromomethylacrylate; ethyl 2-bromomethylacrylate; methyl vinyl ketone; ethyl vinyl ketone; methyl isopropenyl ketone; and ethyl isopropenyl ketone. These additional monomers may be used alone or in combination with one another.

In the (meth)acrylic polymer block (a), the content of the monomer unit formed from any of the additional monomers mentioned above is preferably 10 mol % or less, and more preferably 5 mol % or less with respect to the total monomer units that form the (meth)acrylic polymer block (a).

The number average molecular weight (Mn) of the (meth) acrylic polymer block (a) is not particularly limited. In terms of the ease of handling of the (meth)acrylic block copolymer (A), the number average molecular weight is preferably in the range of 500 to 1,000,000, and more preferably in the range of 1,000 to 300,000. The Mn and the molecular weight distribution as defined herein refer to polystyrene-equivalent number average molecular weight and distribution as determined by gel permeation chromatography (GPC).

The (meth)acrylic block copolymer (A) includes a (meth) acrylic polymer block (b). The (meth)acrylic polymer block (b) is a polymer block consisting of a monomer unit formed by polymerizing a monomer containing a (meth)acrylic acid ester and having no curable functional group.

As used herein, a curable functional group refers to a functional group exhibiting polymerizability. Examples of such a curable functional group include: functional groups having an ethylenic double bond (in particular, an ethylenic double bond represented by the general formula CH$_2$=CR—, where R is an alkyl group or a hydrogen atom) such as (meth)acryloyl, (meth)acryloyloxy, vinyl, allyl, vinylether, vinyloxy, 1,3-dienyl, and styryl groups; epoxy groups; oxetanyl groups; thiol groups; and maleimide groups.

Examples of the (meth)acrylic acid ester that can be used to form the (meth)acrylic polymer block (b) include monofunctional (meth)acrylic acid esters such as methyl (met) acrylate, ethyl (meth)acrylate, n-propyl (meth)acrylate, isopropyl (meth)acrylate, n-butyl (meth)acrylate, t-butyl (meth) acrylate, cyclohexyl (meth)acrylate, 2-ethylhexyl (meth) acrylate, isobornyl (meth)acrylate, dodecyl (meth)acrylate, 3-(trimethoxysilyl)propyl (meth)acrylate, 2-(N,N-dimethylamino)ethyl (meth)acrylate, 2-(N,N-diethylamino)ethyl (meth)acrylate, 2-methoxyethyl (meth)acrylate, phenyl (meth)acrylate, naphthyl (meth)acrylate, 2-(trimethylsilyloxy)ethyl (meth)acrylate, and 3-(trimethylsilyloxy)propyl (meth)acrylate. Among these, preferred are acrylic acid alkyl esters having 4 or more and 20 or less alkyl groups, such as n-butyl acrylate, t-butyl acrylate, 2-ethylhexyl acrylate, and dodecyl acrylate, and methacrylic acid alkyl esters having 6 or more and 20 or less alkyl groups, such as 2-ethylhexyl methacrylate and dodecyl methacrylate. These (meth)acrylic acid esters may be used alone or in combination with one another. The monofunctional (meth)acrylic acid ester used to form the (meth)acrylic polymer block (b) may be the same as or different from the monofunctional (meth)acrylic acid ester used to form the (meth)acrylic polymer block (a). However, they are preferably different from each other.

In the (meth)acrylic polymer block (b), the content of the monomer unit formed from a (meth)acrylic acid ester is preferably 90 mol % or more, and more preferably 95 mol % or more, with respect to the total monomer units that form the (meth)acrylic polymer block (b).

The (meth)acrylic polymer block (b) may include a monomer unit formed from a monomer other than a (meth)acrylic acid ester. Examples of such an additional monomer include: α-alkoxyacrylic acid esters such as methyl α-methoxyacrylate and methyl α-ethoxyacrylate; crotonic acid esters such as methyl crotonate and ethyl crotonate; 3-alkoxyacrylic acid esters such as 3-methoxyacrylic acid esters; (meth) acrylamides such as N-isopropyl (meth)acrylamide, N-t-butyl (meth)acrylamide, N,N-dimethyl (meth)acrylamide, and N,N-diethyl (meth)acrylamide; methyl vinyl ketone; ethyl vinyl ketone; methyl isopropenyl ketone; and ethyl isopropenyl ketone. These additional monomers may be used alone or in combination with one another.

In the (meth)acrylic polymer block (b), the content of the monomer unit formed from any of the additional monomers mentioned above is preferably 10 mol % or less, and more preferably 5 mol % or less, with respect to the total monomer units that form the (meth)acrylic polymer block (b).

The Mn of the (meth)acrylic polymer block (b) is not particularly limited. In terms of, for example, the ease of handling and mechanical properties of the (meth)acrylic block copolymer (A), the Mn is preferably in the range of 3,000 to 2,000,000 and more preferably in the range of 5,000 to 1,000,000.

The molecular weight distribution of the (meth)acrylic block copolymer (A), that is, weight average molecular weight/number average molecular weight (Mw/Mn), is preferably in the range of 1.02 to 2.00, more preferably in the range of 1.05 to 1.80, and even more preferably in the range of 1.10 to 1.50.

The (meth)acrylic block copolymer (A) is a block copolymer in which at least one (meth)acrylic polymer block (a) and at least one (meth)acrylic polymer block (b) are linked together. The number of polymer blocks (a) and the number of polymer blocks (b) and the order of linking these blocks (a) and (b) are not particularly limited. It is preferable that the (meth)acrylic polymer block (a) form at least one end of the (meth)acrylic block copolymer (A) in terms of photo-curability. It is more preferable that the (meth)acrylic block copolymer (A) be a linear polymer in terms of the ease of producing the copolymer (A). It is even more preferable that the copolymer (A) be a diblock copolymer in which one (meth)acrylic polymer block (a) and one (meth)acrylic polymer block (b) are linked together or a triblock copolymer in which one (meth)acrylic polymer block (a) is linked to each of the ends of one (meth)acrylic polymer block (b).

In the (meth)acrylic block copolymer (A), the ratio of the mass of the (meth)acrylic polymer block (a) to the mass of the (meth)acrylic polymer block (b) [(meth)acrylic polymer block (a):(meth)acrylic polymer block (b)] is not particularly limited. The ratio is preferably 90:10 to 5:95, more preferably 80:20 to 7:93, and even more preferably 75:25 to 10:90. When the ratio of the mass of the (meth)acrylic polymer block (a) to the total mass of the (meth)acrylic polymer block (a) and (meth)acrylic polymer block (b) is 5% or more, the dental polymerizable composition of the present invention has a higher cure rate. When the ratio is 90% or less, a cured product obtained from the dental polymerizable composition of the present invention tends to be flexible.

In the (meth)acrylic block copolymer (A), the content of the monomer unit formed from a methacrylic acid ester is preferably 5 to 85 mass %, more preferably 7 to 80 mass %, and even more preferably 10 to 75 mass %. In the (meth) acrylic block copolymer (A), the content of the monomer unit formed from an acrylic acid ester is preferably 15 to 95 mass %, more preferably 20 to 93 mass %, and even more preferably 25 to 90 mass %.

The Mn of the (meth)acrylic block copolymer (A) is not particularly limited. The Mn is preferably in the range of 4,000 to 3,000,000, more preferably in the range of 7,000 to 2,000,000, and even more preferably in the range of 10,000 to 1,000,000, in terms of, for example, the ease of handling and mechanical properties.

The molecular weight distribution of the (meth)acrylic block copolymer (A), that is, weight average molecular weight/number average molecular weight (Mw/Mn), is preferably in the range of 1.02 to 2.00, more preferably in the range of 1.05 to 1.80, and even more preferably in the range of 1.10 to 1.50. The Mw as defined herein refers to a polystyrene-equivalent weight average molecular weight as determined by gel permeation chromatography (GPC).

In the (meth)acrylic block copolymer (A), the content of the partial structure (1) is preferably in the range of 0.1 to 30 mol %, more preferably in the range of 1 to 20 mol %, and even more preferably in the range of 3 to 15 mol % with respect to the total monomer units that form the (meth) acrylic block copolymer (A).

The number of partial structures (1) included in the (meth)acrylic block copolymer (A) is preferably 4 or more and more preferably 8 or more per molecule of the polymer in terms of the cure rate.

The (meth)acrylic block copolymer (A) is obtained by forming a (meth)acrylic polymer block (a) and a (meth) acrylic polymer block (b) in a desired order. The method for producing the (meth)acrylic block copolymer (A) is not particularly limited. Anionic polymerization or radical polymerization is preferred, living anionic polymerization or living radical polymerization is more preferred in terms of polymerization control, and living anionic polymerization is even more preferred. In order to allow the polymerization to proceed smoothly, it is preferable to dry the monomers used in the production of the (meth)acrylic block copolymer (A) in an inert gas atmosphere before the polymerization. A dehydrating agent or a desiccating agent such as calcium hydride, molecular sieves and active alumina are preferably used for the drying treatment.

Examples of the living radical polymerization include a polymerization process using a chain transfer agent such as polysulfide or the like, a polymerization process using a cobalt porphyrin complex, a polymerization process using a nitroxide (see WO 2004/014926 A2), a polymerization process using a high heterocyclic element compound such as an organotellurium compound or the like (see JP 3839829 B2), a reversible addition-fragmentation chain transfer (RAFT) polymerization process (see JP 3639859 B2), and an atom-transfer radical polymerization (ATRP) process (see JP 3040172 B2 and WO 2004/013192 A1). Among these living radical polymerization processes, preferred is an atom-transfer radical polymerization process, and more preferred is an atom-transfer radical polymerization process using, as an initiator, an organic halogen compound or a sulfonyl halide compound and, as a catalyst, a metal complex containing at least one selected from the group consisting of Fe, Ru, Ni, and Cu as a central metal.

Examples of the living anionic polymerization include a living polymerization process using an organic rare earth metal complex as a polymerization initiator (see JP 06-93060 A), a living anionic polymerization process performed using an organic alkali metal compound as a polymerization initiator in the presence of a mineral acid salt such as a salt of an alkali metal or an alkaline earth metal (see JP 05-507737 T), and a living anionic polymerization process performed using an organic alkali metal compound as a polymerization initiator in the presence of an organoaluminum compound (see JP 11-335432 A and WO 2013/141105 A1). Among these living anionic polymerization processes, preferred is a living anionic polymerization process performed using an organic alkali metal compound as a polymerization initiator in the presence of an organoaluminum compound in terms of direct and efficient formation of a (meth)acrylic polymer block (a), and more preferred is a living anionic polymerization process performed using an organolithium compound as a polymerization initiator in the presence of an organoaluminum compound and a Lewis base.

A specific example of the method for producing the (meth)acrylic block copolymer (A) used in the present invention is a production method including: a step (I) of anionically polymerizing a (meth)acrylic acid ester containing 5 to 100 mol % of a di(meth)acrylate (3) in the presence of an organolithium compound, a Lewis base, and an organoaluminum compound having in the molecule a chemical structure represented by the general formula (4) Al—O—Ar, where Ar represents an aromatic ring; a step [II] of adding and anionically polymerizing a monofunctional (meth)acrylic acid ester after the step [I]; and optionally a step [III] of adding and anionically polymerizing a (meth) acrylic acid ester containing the di(meth)acrylate (3) after the step [II]. Preferably, the method includes a step [IV] of terminating the polymerization reaction using a polymerization terminator.

[Step (I)]

In the step [I], a (meth)acrylic polymer block (a) is formed by anionic polymerization.

Examples of the organolithium compound include t-butyllithium, 1,1-dimethylpropyllithium, 1,1-diphenylhexyllithium, 1,1-diphenyl-3-methylpentyllithium, ethyl α-lithioisobutyrate, butyl α-lithioisobutyrate, methyl α-lithioisobutyrate, isopropyllithium, sec-butyllithium, 1-methylbutyllithium, 2-ethylpropyllithium, 1-methylpentyllithium, cyclohexyllithium, diphenylmethyllithium, α-methylbenzyllithium, methyllithium, n-propyllithium, n-butyllithium, and n-pentyllithium. Among these, in terms of availability and anionic polymerization initiation ability, preferred are organolithium compounds having 3 to 40 carbon atoms and having a chemical structure in which the anionic center is a secondary carbon atom, such as isopropyllithium, sec-butyllithium, 1-methylbutyllithium, 1-methylpentyllithium, cyclohexyllithium, diphenylmethyllithium, and α-methylbenzyllithium, and particularly preferred is sec-butyllithium. These organolithium compounds may be used alone or in combination with one another.

The amount of an organolithium compound to be used can be determined by the ratio of the organolithium compound to the amount of monomers to be used depending on the desired Mn of the (meth)acrylic block copolymer (A).

The organoaluminum compound mentioned above may be selected appropriately according to, for example, the types of the monomers to be used (i.e., the di(meth)acrylate (3) and as an optional components, a mono(meth)acrylate and an additional monomer mentioned above). In terms of the polymerization rate, polymerization initiation efficiency, and stability of polymer-end anions, it is preferable to use an organoaluminum compound (hereinafter referred to as an organoaluminum compound (4-1)) represented by the following general formula (4-1):

$$AlR^7(R^8)(R^9) \quad (4\text{-}1),$$

where $R^7$ represents a monovalent saturated hydrocarbon group, a monovalent aromatic hydrocarbon group, an alkoxy group, an aryloxy group, or an N,N-disubstituted amino group, and $R^8$ and $R^9$ each independently represent an aryloxy group, or $R^8$ and $R^9$ in combination form an arylenedioxy group, or to use an organoaluminum compound (hereinafter referred to an organoaluminum compound (4-2)) represented by the following general formula (4-2):

$$AlR^{10}(R^{11})(R^{12}) \quad (4\text{-}2),$$

where $R^{10}$ represents an aryloxy group, and $R^{11}$ and $R^{12}$ each independently represent a monovalent saturated hydrocarbon group, a monovalent aromatic hydrocarbon group, an alkoxy group, or an N,N-disubstituted amino group.

Examples of the aryloxy group represented by $R^7$, $R^8$, $R^9$, and $R^{10}$ each independently in the above general formulae (4-1) and (4-2) include phenoxy, 2-methylphenoxy, 4-methylphenoxy, 2,6-dimethylphenoxy, 2,4-di-t-butylphenoxy, 2,6-di-t-butylphenoxy, 2,6-di-t-butyl-4-methylphenoxy, 2,6-di-t-butyl-4-ethylphenoxy, 2,6-diphenylphenoxy, 1-naphthoxy, 2-naphthoxy, 9-phenanthryloxy, 1-pyrenyloxy, and 7-methoxy-2-naphthoxy groups.

Examples of the arylenedioxy group represented by $R^8$ and $R^9$ in combination in the above general formula (4-1) include functional groups obtained by removing hydrogen atoms from two phenolic hydroxyl groups in compounds each having two phenolic hydroxyl groups, such as 2,2'-biphenol, 2,2'-methylenebisphenol, 2,2'-methylenebis(4-methyl-6-t-butylphenol), (R)-(+)-1,1'-bi-2-naphthol, and (S)-(–)-1,1'-bi-2-naphthol.

In the aryloxy groups and arylenedioxy groups mentioned above, one or more hydrogen atoms may be substituted by substituents. Examples of such substituents include: alkoxy groups such as methoxy, ethoxy, isopropoxy, and t-butoxy groups; and halogen atoms such as chlorine and bromine atoms.

Examples of the monovalent saturated hydrocarbon groups represented by $R^7$, $R^{11}$, and $R^{12}$ each independently in the above general formulae (4-1) and (4-2) include: alkyl groups such as methyl, ethyl, n-propyl, isopropyl, n-butyl, isobutyl, sec-butyl, t-butyl, 2-methylbutyl, 3-methylbutyl, n-octyl, and 2-ethylhexyl groups; and cycloalkyl groups such as a cyclohexyl group. Examples of the aromatic hydrocarbon groups represented by $R^7$, $R^{11}$, and $R^{12}$ each independently include aryl groups such as a phenyl group; and aralkyl groups such as a benzyl group. Examples of the alkoxy groups represented by $R^7$, $R^{11}$, and $R^{12}$ each independently include methoxy, ethoxy, isopropoxy, and t-butoxy groups. Examples of the N,N-disubstituted amino groups represented by $R^7$, $R^{11}$, and $R^{12}$ each independently include dialkylamino groups such as dimethylamino, diethylamino, and diisopropylamino groups; and bis(trimethylsilyl)amino groups. In the monovalent saturated hydrocarbon groups, monovalent aromatic hydrocarbon groups, alkoxy groups, and N,N-disubstituted amino groups mentioned above, one or more hydrogen atoms may be substituted by substituents. Examples of such substituents include: alkoxy groups such as methoxy, ethoxy, isopropoxy, and t-butoxy groups; and halogen atoms such as chlorine and bromine atoms.

Examples of the organoaluminum compound (4-1) include ethylbis(2,6-di-t-butyl-4-methylphenoxy)aluminum, ethylbis(2,6-di-t-butylphenoxy)aluminum, ethyl[2,2'-methylenebis(4-methyl-6-t-butylphenoxy)]aluminum, isobutylbis(2,6-di-t-butyl-4-methylphenoxy)aluminum, isobutylbis(2,6-di-t-butylphenoxy)aluminum, isobutyl[2,2'-methylenebis(4-methyl-6-t-butylphenoxy)]aluminum, n-octylbis(2,6-di-t-butyl-4-methylphenoxy)aluminum, n-octylbis(2,6-di-t-butylphenoxy)aluminum, n-octyl[2,2'-methylenebis(4-methyl-6-t-butylphenoxy)]aluminum, methoxybis(2,6-di-t-butyl-4-methylphenoxy)aluminum, methoxybis(2,6-di-t-butylphenoxy)aluminum, methoxy[2,2'-methylenebis(4-methyl-6-t-butylphenoxy)]aluminum, ethoxybis(2,6-di-t-butyl-4-methylphenoxy)aluminum, ethoxybis(2,6-di-t-butylphenoxy)aluminum, ethoxy[2,2'-methylenebis(4-methyl-6-t-butylphenoxy)]aluminum, isopropoxybis(2,6-di-t-butyl-4-methylphenoxy)aluminum, isopropoxybis(2,6-di-t-butylphenoxy)aluminum, isopropoxy[2,2'-methylenebis(4-methyl-6-t-butylphenoxy)]aluminum, t-butoxybis(2,6-di-t-butyl-4-methylphenoxy)aluminum, t-butoxybis(2,6-di-t-butylphenoxy)aluminum, t-butoxy[2,2'-methylenebis(4-methyl-6-t-butylphenoxy)]aluminum, tris(2,6-di-t-butyl-4-methylphenoxy)aluminum, and tris(2,6-diphenylphenoxy)aluminum. Among these, in terms of the polymerization initiation efficiency, living properties of polymer end anions, availability, and ease of handling, preferred are isobutylbis(2,6-di-t-butyl-4-methylphenoxy)aluminum, isobutylbis(2,6-di-t-butylphenoxy)aluminum, isobutyl[2,2'-methylenebis(4-methyl-6-t-butylphenoxy)]aluminum, and the like.

Examples of the organoaluminum compound (4-2) include diethyl(2,6-di-t-butyl-4-methylphenoxy)aluminum, diethyl(2,6-di-t-butylphenoxy)aluminum, diisobutyl(2,6-di-t-butyl-4-methylphenoxy)aluminum, diisobutyl(2,6-di-t-butylphenoxy)aluminum, di-n-octyl(2,6-di-t-butyl-4-methylphenoxy)aluminum, and di-n-octyl(2,6-di-t-butylphenoxy)aluminum. These organoaluminum compounds may be used alone or in combination with one another.

The amount of the organoaluminum compound to be used may be selected appropriately according to the type of a solvent and other various polymerization conditions. In terms of the polymerization rate, the amount of the organoaluminum compound is generally preferably in the range of 1.0 to 10.0 mol, more preferably in the range of 1.1 to 5.0 mol, and even more preferably in the range of 1.2 to 4.0 mol, per 1 mol of the organolithium compound. When the amount of the organoaluminum compound used is more than 10.0 mol per 1 mole of the organolithium compound, the use of the organoaluminum compound tends to be economically disadvantageous. When the amount of the organoaluminum compound used is less than 1.0 mol, the polymerization initiation efficiency tends to decrease.

Examples of the Lewis base mentioned above include compounds having an ether bond and/or a tertiary amine structure in the molecule.

Examples of the compound having an ether bond in the molecule and used as the Lewis base include ethers. In terms of the high polymerization initiation efficiency and living properties of polymer end anions, the ether is preferably a cyclic ether having two or more ether bonds in the molecule or an acyclic ether having one or more ether bonds in the molecule. Examples of the cyclic ether having two or more ether bonds in the molecule include crown ethers such as 12-crown-4, 15-crown-5, and 18-crown-6. Examples of the acyclic ether having one or more ether bonds in the molecule include: acyclic monoethers such as dimethyl ether, diethyl ether, diisopropyl ether, dibutyl ether, and anisole; acyclic diethers such as 1,2-dimethoxyethane, 1,2-diethoxyethane, 1,2-diisopropoxyethane, 1,2-dibutoxyethane, 1,2-diphenoxyethane, 1,2-dimethoxypropane, 1,2-diethoxypropane, 1,2-diisopropoxypropane, 1,2-dibutoxypropane, 1,2-diphenoxypropane, 1,3-dimethoxypropane, 1,3-diethoxypropane, 1,3-diisopropoxypropane, 1,3-dibutoxypropane, 1,3-diphenoxypropane, 1,4-dimethoxybutane, 1,4-diethoxybutane, 1,4-diisopropoxybutane, 1,4-dibutoxybutane, and 1,4-diphenoxybutane; and acyclic polyethers such as diethylene glycol dimethyl ether, dipropylene glycol dimethyl ether, dibutylene glycol dimethyl ether, diethylene glycol diethyl ether, dipropylene glycol diethyl ether, dibutylene glycol diethyl ether, triethylene glycol dimethyl ether, tripropylene glycol dimethyl ether, tributylene glycol dimethyl ether, triethylene glycol diethyl ether, tripropylene glycol diethyl ether, tributylene glycol diethyl ether, tetraethylene glycol dimethyl ether, tetrapropylene glycol dimethyl ether, tetrabutylene glycol dimethyl ether, tetraethylene glycol diethyl ether, tetrapropylene glycol diethyl ether, and tetrabutylene glycol diethyl ether. Among these, in terms of suppression of side reactions, availability, etc., preferred are acyclic ethers having one or two ether bonds in the molecule, and more preferred is diethyl ether or 1,2-dimethoxyethane.

Examples of the compound having a tertiary amine structure in the molecule and used as the Lewis base include tertiary polyamines. Tertiary polyamines refer to compounds having two or more tertiary amine structures in the molecule. Examples of the tertiary polyamine include chain polyamines such as N,N,N',N'-tetramethylethylenediamine, N,N,N',N'-tetraethylethylenediamine, N,N,N',N'',N''-pentamethyldiethylenetriamine, 1,1,4,7,10,10-hexamethyltriethylenetetramine, and tris[2-(dimethylamino)ethyl]amine; nonaromatic heterocyclic compounds such as 1,3,5-trimethylhexahydro-1,3,5-triazine, 1,4,7-trimethyl-1,4,7-triazacyclononane, and 1,4,7,10,13,16-hexamethyl-1,4,7,10,13,16-hexaazacyclooctadecane; and aromatic heterocyclic compounds such as 2,2'-bipyridyl and 2,2':6',2''-terpyridine.

These Lewis bases may be used alone or in combination with one another.

In terms of the polymerization initiation efficiency, stability of polymer end anions, etc., the amount of the Lewis base to be used is preferably in the range of 0.3 to 5.0 mol, more preferably in the range of 0.5 to 3.0 mol, and even more preferably in the range of 1.0 to 2.0 mol, per 1 mol of the organolithium compound. When the amount of the Lewis base used is more than 5.0 mol per 1 mole of the organolithium compound, the use of the Lewis base tends to be economically disadvantageous. When the amount of the Lewis base used is less than 0.3 mol, the polymerization initiation efficiency tends to decrease.

The amount of the Lewis base to be used is preferably in the range of 0.2 to 1.2 mol, and more preferably in the range of 0.3 to 1.0 mol, per 1 mol of the organoaluminum compound.

In order to control the living anionic polymerization temperature and to make the system homogeneous to allow the polymerization to proceed smoothly, the polymerization is preferably carried out in the presence of an organic solvent. In terms of the safety, separability from water used in washing of the reaction solution having undergone polymerization, ease of recovery and reuse, preferred examples of the organic solvent include hydrocarbons such as toluene, xylene, cyclohexane, and methylcyclohexane; halogenated hydrocarbons such as chloroform, methylene chloride, and carbon tetrachloride; and esters such as dimethyl phthalate. These organic solvents may be used alone or in combination with one another. In order to allow the polymerization to proceed smoothly, it is preferable to dry and degas the organic solvent in an inert gas atmosphere before the polymerization.

In the living anionic polymerization described above, an additional additive may be added to the reaction system, if necessary. Examples of such an additional additive include: inorganic salts such as lithium chloride; metal alkoxides such as lithium methoxyethoxyethoxide and potassium t-butoxide; tetraethylammonium chloride; and tetraethylphosphonium bromide.

It is preferable to carry out the living anionic polymerization at −30 to 25° C. When the temperature is lower than −30° C., the polymerization rate decreases and tends to cause a decrease in productivity. On the other hand, when the temperature is higher than 25° C., it tends to be difficult to carry out the polymerization with good living properties.

It is preferable to carry out the living anionic polymerization in an atmosphere of an inert gas such as nitrogen, argon, or helium. It is also preferable to carry out the living anionic polymerization with sufficient stirring so as to make the reaction system homogeneous. In order to allow the living anionic polymerization to proceed smoothly, it is preferable to dry the monomers used in an inert gas atmosphere before the polymerization. A dehydrating agent or a desiccating agent such as calcium hydride, molecular sieves and active alumina are preferably used for the drying treatment.

In the living anionic polymerization, when an organolithium compound, an organoaluminum compound, a Lewis base, and a monomer are added to an anionic polymerization reaction system, it is preferable to add them in such a manner that the Lewis base be brought into contact with the organoaluminum compound before contact with the organolithium compound. The organoaluminum compound may be added to the anionic polymerization reaction system before or simultaneously with the addition of the monomer. When the organoaluminum compound is added to the anionic polymerization reaction system simultaneously with the addition of the monomer, the organoaluminum compound may be mixed with the monomer before the addition.

In the step [I], the polymerization initiation efficiency (F1) is preferably 85% or more, more preferably 90% or more, and even more preferably 95% or more, because the resulting dental polymerizable composition has good discharging and forming properties, high stain resistance, and high flexibility. The polymerization initiation efficiency (F1) is calculated by the method described in EXAMPLES below.

Step [II]

In the step [II], a monofunctional (meth)acrylic acid ester is added to form a (meth)acrylic polymer block (b) by living anionic polymerization. In addition to the monomers used in the step [II] (that is, a monofunctional (meth)acrylic acid ester and an additional monomer as an optional component), an organoaluminum compound, a Lewis base, and an organic solvent may be added to the living anionic polymerization reaction system. Examples of such organoaluminum compound, Lewis base, and organic solvent include those mentioned above as examples of organoaluminum compounds, Lewis bases, and organic solvents that may be used in the step [I]. The amounts of these organoaluminum compound, Lewis base, and organic solvent may be selected appropriately according to the type of the solvent and other various polymerization conditions. The living anionic polymerization can be carried out under the same conditions as those that can be used in the step [I]. In order to adjust the polymerization reaction and to increase the blocking efficiency of the resulting copolymer (A), the rate of adding the monofunctional (meth)acrylic acid ester may be 5 to 30 ml/min or 7 to 20 ml/min. The blocking efficiency (F2) from the end of the step [I] to the end of the step [II] is preferably 50% or more, more preferably 70% or more, and even more preferably 90% or more, because the elasticity can be increased, a molecular weight distribution within a predetermined range can be obtained, and the resulting dental polymerizable composition has good discharging and forming properties, high stain resistance, and high flexibility. The blocking efficiency (F2) is calculated by the method described in EXAMPLES below.

Step [III]

In the step [III], after the step [II], a (meth)acrylic acid ester containing a di(meth)acrylate (3) is added to the reaction solution obtained in the step [II] to form a (meth)acrylic polymer block (a) by living anionic polymerization, in the same manner as in the step [I]. In the step [III], heating may be performed, if necessary. The blocking efficiency can be increased by heating. The heating temperature is not particularly limited, and it is preferably 50° C. or lower, and more preferably 40° C. or lower.

Step [IV]

The living anionic polymerization may be terminated by adding a polymerization terminator to the reaction solution. Examples of the polymerization terminator include protic compounds such as: methanol; methanol solutions of acetic acid or hydrochloric acid; and aqueous solutions of acetic acid or hydrochloric acid. The amount of the polymerization terminator to be used is generally preferably in the range of 1 to 100 mol per 1 mol of the organolithium compound used.

After the termination of the anionic polymerization, the (meth)acrylic block copolymer (A) can be separated and obtained from the reaction solution by a commonly-known method. Examples of such a commonly-known method include: a method in which the reaction solution is poured into a poor solvent for the (meth)acrylic block copolymer (A) to precipitate the (meth)acrylic block copolymer (A); and a method in which the organic solvent is distilled off from the reaction solution to obtain the (meth)acrylic block copolymer (A).

When the (meth)acrylic block copolymer (A) thus separated and obtained contains metal components derived from the organolithium compound and the organoaluminum compound, the metal components may cause a decrease in the physical properties of the (meth)acrylic block copolymer (A). It is therefore preferable to remove the metal components derived from the organolithium compound and the organoaluminum compound after the termination of the anionic polymerization. Such metal components can be removed effectively by subjecting the block copolymer (A) to a process such as washing with an acidic aqueous solution or adsorption using an adsorbent such as an ion exchange resin, Celite, active carbon, or the like. Examples of the acidic aqueous solution that may be used include hydrochloric acid, aqueous sulfuric acid solution, aqueous nitric acid solution, aqueous acetic acid solution, aqueous propionic acid solution, and aqueous citric acid solution.

In the production of the (meth)acrylic block copolymer (A), as a method for introducing a curable functional group having the partial structure (1), the above-described method in which a monomer containing the di(meth)acrylate (3) is polymerized to form a (meth)acrylic polymer block (a) is used, and in addition, a method in which a polymer block having a partial structure serving as the precursor of the partial structure (1) (hereinafter referred to as a "precursor structure") is formed and then the precursor structure is converted to the partial structure (1) also can be used. The polymer block having a precursor structure can be obtained by polymerizing a polymerizable functional group and a monomer containing a compound having the precursor structure. Examples of such a polymerizable functional group include styryl, 1,3-dienyl, vinyloxy, and (meth)acryloyl groups, and (meth)acryloyl group is preferred. Examples of the precursor structure include a hydroxy group and a hydroxy group protected by a protecting group (such as a silyloxy, acyloxy, or alkoxy group), an amino group and an amino group protected by a protecting group, a thiol group and a thiol group protected by a protecting group, and an isocyanate group.

When a polymer block having a hydroxy group as a precursor structure is used, the (meth)acrylic polymer block (a) can be formed by reacting the polymer block with a compound having the partial structure (1) and a partial structure (such as a carboxyl group, ester, or carbonyl halide) capable of reacting with a hydroxy group. When a polymer block having a hydroxy group protected by a protecting group as a precursor structure is used, the (meth) acrylic polymer block (a) can be formed in the same manner as described above after the protecting group is removed from the hydroxy group.

When a polymer block having an amino group as a precursor structure is used, the (meth)acrylic polymer block (a) can be formed by reacting the polymer block with a compound having the partial structure (1) and a partial structure (such as a carboxyl group, carboxylic acid anhydride, ester, carbonyl halide, aldehyde group, or isocyanate group) capable of reacting with an amino group. When a polymer block having an amino group protected by a protecting group as a precursor structure is used, the (meth) acrylic polymer block (a) can be formed in the same manner as described above after the protecting group is removed from the amino group.

When a polymer block having a thiol group as a precursor structure is used, the (meth)acrylic polymer block (a) can be formed by reacting the polymer block with a compound having the partial structure (1) and a partial structure (such as a carboxyl group, carboxylic acid anhydride, ester, carbonyl halide, isocyanate group, or a carbon-carbon double bond) capable of reacting with a thiol group. When a polymer block having a thiol group protected by a protecting group as a precursor structure is used, the (meth)acrylic polymer block (a) can be formed in the same manner as described above after the protecting group is removed from the thiol group.

When a polymer block having an isocyanate group as a precursor structure is used, the (meth)acrylic polymer block (a) can be formed by reacting the polymer block with a compound having the partial structure (1) and a partial structure (such as hydroxy group or amino group) capable of reacting with an isocyanate group.

In the production of the (meth)acrylic block copolymer (A), as a method for forming a (meth)acrylic polymer block (a), a method in which a monomer containing a di(meth) acrylate (3) is polymerized, typically a method in which a monomer containing a di(meth)acrylate (3) is anionically polymerized, is preferred because a curable functional group (2) can be introduced easily and directly using such a monomer.

The dental polymerizable composition of the present invention includes a polymerizable monomer (B). As the polymerizable monomer (B), a radical polymerizable monomer is suitably used. Examples of the radical polymerizable monomer include esters of α-cyanoacrylic acid, (meth) acrylic acid, α-halogenated acrylic acid, crotonic acid, cinnamic acid, sorbic acid, maleic acid, and itaconic acid; (meth)acrylamides; vinyl esters; vinyl ethers; and styrene derivatives. Among these, (meth)acrylic acid esters are preferred in terms of the miscibility with the (meth)acrylic block copolymer (A). The polymerizable monomer (B) may be a monofunctional, bifunctional, or tri- or higher-functional polymerizable monomer.

Examples of the monofunctional polymerizable monomer (B) include methyl (met)acrylate, ethyl (meth)acrylate, n-propyl (meth)acrylate, isopropyl (meth)acrylate, n-butyl (meth)acrylate, t-butyl (meth)acrylate, 2-ethylhexyl (meth) acrylate, dodecyl (meth)acrylate, cetyl (meth)acrylate, stearyl (meth)acrylate, 2,3-dibromopropyl (meth)acrylate, cyclohexyl (meth)acrylate, isobornyl (meth)acrylate, phenyl (meth)acrylate, naphthyl (meth)acrylate, benzyl (meth)acrylate, 2-methoxyethyl (meth)acrylate, 2-ethoxyethyl (meth) acrylate, 2-butoxyethyl (meth)acrylate, 2-hydroxyethyl (meth)acrylate, 2-hydroxypropyl (meth)acrylate, 3-hydroxypropyl (meth)acrylate, 2-hydroxybutyl (meth)acrylate, 4-hydroxybutyl (meth)acrylate, 6-hydroxyhexyl (meth) acrylate, 10-hydroxydecyl (meth)acrylate, propylene glycol mono(meth)acrylate, glycerol mono(meth)acrylate, erythritol mono(meth)acrylate, 2-aminoethyl (meth)acrylate, 2-(N, N-dimethylamino)ethyl (meth)acrylate, 2-(N,N-diethylamino)ethyl (meth)acrylate, glycidyl (meth)acrylate, 3-(trimethoxysilyl)propyl (meth)acrylate, 2-(trimethylsilyloxy)ethyl (meth)acrylate, 3-(trimethylsilyloxy)propyl (meth)acrylate, γ-((meth)acryloyloxypropyl)trimethoxysilane, 11-(meth)acryloyloxyundecyltrimethoxysilane, N-methylol (meth)acrylamide, N-hydroxyethyl (meth)acrylamide, N,N-(dihydroxyethyl) (meth)acrylamide, and (meth)acrylamides. Among these, methyl (meth)acrylate, ethyl (meth)acrylate, n-butyl (meth)acrylate, sec-butyl (meth)acrylate, t-butyl (meth)acrylate, isobutyl (meth)acrylate, n-hexyl (meth)acrylate, cyclohexyl (meth)acrylate, and isobornyl (meth)acrylate are preferred in that they have good miscibility with the (meth)acrylic block copolymer (A) and contribute to the good flexibility of the resulting cured product. Methyl (meth)acrylate, t-butyl (meth)acrylate, and isobornyl (meth)acrylate are more preferred in terms of the toughness of the resulting cured product.

Examples of the difunctional polymerizable monomer (B) include 2,2-bis((meth)acryloyloxyphenyl)propane, 2,2-bis [4-(3-acryloyloxy-2-hydroxypropoxyphenyl]propane, 2,2-bis[4-(3-methacryloyloxy-2-hydroxypropoxy)phenyl]propane (commonly called "Bis-GMA"), 2,2-bis(4-(meth) acryloyloxyethoxyphenyl)propane, 2,2-bis(4-(meth) acryloyloxypolyethoxyphenyl)propane, 2,2-bis(4-(meth) acryloyloxydiethoxyphenyl)propane, 2,2-bis(4-(meth) acryloyloxytetraethoxyphenyl)propane, 2,2-bis(4-(meth) acryloyloxypentaethoxyphenyl)propane, 2,2-bis(4-(meth) acryloyloxydipropoxyphenyl)propane, 2-(4-(meth) acryloyloxydiethoxyphenyl)-2-(4-(meth) acryloyloxyethoxyphenyl)propane, 2-(4-(meth) acryloyloxydiethoxyphenyl)-2-(4-(meth) acryloyloxytriethoxyphenyl)propane, 2-(4-(meth) acryloyloxydipropoxyphenyl)-2-(4-(meth) acryloyloxytriethoxyphenyl)propane, 2,2-bis(4-(meth) acryloyloxypropoxyphenyl)propane, 2,2-bis(4-(meth) acryloyloxyisopropoxyphenyl)propane, 1,4-bis(2-(meth) acryloyloxyethyl)pyromellitate, glycerol di(meth)acrylate, ethylene glycol di(meth)acrylate, diethylene glycol di(meth) acrylate, triethylene glycol di(meth)acrylate, propylene glycol di(meth)acrylate, butylene glycol di(meth)acrylate, neopentyl glycol di(meth)acrylate, polyethylene glycol di(meth) acrylate, 1,3-butanediol di(meth)acrylate, 1,4-butanediol di(meth)acrylate, 1,6-hexanediol di(meth)acrylate, 2-ethyl-1,6-hexanediol di(meth)acrylate, 1,9-nonanediol di(meth) acrylate, 1,10-decanediol di(meth)acrylate, 1,2-bis(3-methacryloyloxy-2-hydroxypropoxy)ethane, and 2,2,4-trimethylhexamethylenebis(2-carbamoyloxyethyl) dimethacrylate (commonly called "UDMA"). Among these, 2,2-bis(4-(meth)acryloyloxypolyethoxyphenyl)propane, glycerol di(meth)acrylate, triethylene glycol di(meth)acrylate, neopentyl glycol di(meth)acrylate, 1,4-butanediol di(meth)acrylate, 1,6-hexanediol di(meth)acrylate, 2-ethyl-1,6-hexanediol di(meth)acrylate, 1,9-nonanediol di(meth)acrylate, 1,10-decanediol di(meth)acrylate, and 2,2,4-trimethylhexamethylenebis(2-carbamoyloxyethyl) di(meth)acrylate are preferred in terms of the miscibility with the (meth)acrylic block copolymer (A) and the strength of the resulting cured product.

Examples of the tri- or higher-functional polymerizable monomer (B) include trimethylolpropane tri(meth)acrylate, trimethylolethane tri(meth)acrylate, trimethylolmethane tri(meth)acrylate, pentaerythritol tri(meth)acrylate, pentaerythritol tetra(meth)acrylate, dipentaerythritol penta(meth)acrylate, N,N-(2,2,4-trimethylhexamethylene)bis[2-(aminocarboxy)propane-1,3-diol]tetramethacrylate, and 1,7-diacryloyloxy-2,2,6,6-tetraacryloyloxymethyl-4-oxyheptane. Among these, trimethylolpropane tri(meth)acrylate is preferred in that it has good miscibility with the (meth)acrylic block copolymer (A).

A polyfunctional (i.e., difunctional or tri- or higher-functional) polymerizable monomer and a monofunctional polymerizable monomer may be used in combination as the polymerizable monomer (B).

When the dental polymerizable composition of the present invention is used as a dental cement, the content of the polyfunctional polymerizable monomer is preferably 10 to 100 mass %, more preferably 20 to 100 mass %, and even more preferably 40 to 100 mass % with respect to the total amount of the polymerizable monomer (B). When the content of the polyfunctional polymerizable monomer is 10 mass % or more, a cured product of the dental polymerizable composition has high toughness and is thus resistant to fracture.

When the dental polymerizable composition of the present invention is used as a mobile tooth fixing material or a dental self-adhesive composite resin, the content of the polyfunctional polymerizable monomer is preferably 10 to 100 mass %, more preferably 50 to 99 mass %, even more preferably 60 to 98.5 mass %, and particularly preferably 65 to 97.5 mass % with respect to the total amount of the polymerizable monomer (B) in that a cured product has high toughness and is thus resistant to fracture.

When the dental polymerizable composition of the present invention is used as a denture liner, the content of the polyfunctional polymerizable monomer is preferably 1 to 75 mass %, more preferably 2.5 to 50 mass %, and even more preferably 5 to 25 mass % with respect to the total amount of the polymerizable monomer (B). When the content of the polyfunctional polymerizable monomer is 75 mass % or less, a cured product of the dental polymerizable composition has high flexibility.

The total amount of the polymerizable monomer (B), as defined herein, refers to the total amount of the polymerizable monomer (B) contained in the whole dental polymerizable composition. For example, when the dental polymerizable composition of the present invention is provided in a two-component form, the total amount of the polymerizable monomer (B) refers to the sum of the mass of the polymerizable monomer (B) contained in one component and the mass of the polymerizable monomer (B) contained in the other component.

When the dental polymerizable composition of the present invention is used as a mobile tooth fixing material or a self-adhesive composite resin, the polymerizable composition preferably includes, as the polymerizable monomer (B), a polymerizable monomer having an acid group such as a phosphoric acid group, a pyrophosphoric acid group, a thiophosphoric acid group, a phosphonic acid group, a sulfonic acid group, or a carboxylic acid group, to obtain bond strength to teeth, bones, and metals. The polymerizable composition more preferably includes a polymerizable monomer having a phosphoric acid group or a phosphonic acid group and even more preferably contains a polymerizable monomer having a phosphoric acid group, in that such an acid group-containing polymerizable monomer has good miscibility with the (meth)acrylic block copolymer (A). When the dental polymerizable composition of the present invention is used as a dental cement or a denture liner, the polymerizable composition may be free of such an acid group-containing polymerizable monomer.

Examples of such a phosphoric acid group-containing polymerizable monomer that may be used as the polymerizable monomer (B) include: 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, bis[2-(meth)acryloyloxyethyl]hydrogen phosphate, bis[4-(meth)acryloyloxybutyl] hydrogen phosphate, bis[6-(meth)acryloyloxyhexyl] hydrogen phosphate, bis[8-(meth)acryloyloxyoctyl]hydrogen phosphate, bis[9-(meth)acryloyloxynonyl] hydrogen phosphate, bis[10-(meth)acryloyloxydecyl] hydrogen phosphate, 1,3-di(meth)acryloyloxypropyl dihydrogen phosphate, 2-(meth)acryloyloxyethylphenyl hydrogen phosphate, 2-(meth)acryloyloxyethyl-2-bromoethyl hydrogen phosphate, and bis[2-(meth)acryloyloxy-(1-hydroxymethyl)ethyl] hydrogen phosphate; and their salts (such as halides, alkali metal salts, and ammonium salts). Among these, preferred are polymerizable monomers having an alkylene group having 6 to 20 carbon atoms in the main chain such as 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyeicosyl dihydrogen phosphate, bis[6-(meth)acryloyloxyhexyl]hydrogen phosphate, bis[8-(meth)acryloyloxyoctyl] hydrogen phosphate, bis[9-(meth)acryloyloxynonyl] hydrogen phosphate, bis[10-(meth)acryloyloxydecyl]hydrogen phosphate, and their salts. More preferred are polymerizable monomers having an alkylene group having 8 to 12 carbon atoms in the main chain such as 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, bis[8-(meth)acryloyloxyoctyl] hydrogen phosphate, bis[9-(meth)acryloyloxynonyl] hydrogen phosphate, bis[10-(meth)acryloyloxydecyl]hydrogen phosphate, and their salts.

The content of the acid group-containing polymerization monomer (B) is not particularly limited. The content of the acid group-containing polymerizable monomer (B) is preferably 1 to 50 mass %, more preferably 1.5 to 40 mass %, even more preferably 2.5 to 35 mass %, and particularly preferably 5 to 33 mass % with respect to the total amount of the polymerizable monomer (B). When the content is 1 mass % or more, the dental polymerizable composition of the present invention has good bond strength. When the content is 50 mass % or less, the dental polymerizable composition of the present invention has good miscibility.

The dental polymerizable composition of the present invention may include a fluorine atom-containing (meth)acrylic acid ester as the polymerizable monomer (B) for the purpose of increasing the resistance to staining by coloring matters. Examples of such a fluorine atom-containing (meth)acrylic acid ester include 2,2,2-trifluoroethyl (meth)acrylate, 2,2,3,3,3-pentafluoropropyl (meth)acrylate, 2-(perfluorobutyl)ethyl (meth)acrylate, 3-(perfluorobutyl)-2-hydroxypropyl (meth)acrylate, 2-(perfluorohexyl)ethyl (meth)acrylate, 3-(perfluorohexyl)-2-hydroxypropyl (meth)acrylate, 3-(perfluoro-3-methylbutyl)-2-hydroxypropyl (meth)acrylate, 1H,1H,3H-tetrafluoropropyl (meth)acrylate, 1H,1H,5H-octafluoropentyl (meth)acrylate, 1H,1H,7H-dodecafluoroheptyl (meth)acrylate, 1H-1-(trifluoromethyl)trifluoroethyl (meth)acrylate, and 1H,1H,3H-hexafluorobutyl (meth)acrylate.

The content of such a fluorine atom-containing (meth)acrylic acid ester is not particularly limited. In terms of the stain resistance, the content thereof is preferably 20 to 100 mass %, more preferably 30 to 100 mass %, even more preferably 40 to 100 mass %, and particularly preferably 40 to 95 mass % with respect to the total amount of the polymerizable monomer (B).

In terms of the flexibility and discharging force, the content of the polymerizable monomer (B) in the dental polymerizable composition of the present invention is preferably 10 to 95 mass %, more preferably 15 to 90 mass %, and even more preferably 15 to 80 mass %.

When the dental polymerizable composition of the present invention is used as a mobile tooth fixing material, the content of the polymerizable monomer (B) in the dental polymerizable composition is preferably 15 to 95 mass %, more preferably 25 to 90 mass %, and even more preferably 25 to 85 mass %.

When the dental polymerizable composition of the present invention is used as a denture liner, the content of the polymerizable monomer (B) in the dental polymerizable composition is preferably 10 to 90 mass %, more preferably 15 to 80 mass %, and even more preferably 15 to 50 mass %.

When the dental polymerizable composition of the present invention is used as a dental cement, the content of the polymerizable monomer (B) in the dental polymerizable composition is preferably 10 to 95 mass %, more preferably 15 to 90 mass %, and even more preferably 20 to 60 mass %. When such a dental cement is used for temporary cementation, the content of the polymerizable monomer (B) in the dental polymerizable composition is preferably 10 to 80 mass %, more preferably 15 to 70 mass %, and even more preferably 20 to 50 mass %.

When the dental polymerizable composition of the present invention is used as a dental self-adhesive composite resin, the content of the polymerizable monomer (B) in the dental polymerizable composition is preferably 12 to 85 mass %, more preferably 17 to 60 mass %, and even more preferably 17 to 50 mass %.

When the dental polymerizable composition of the present invention is used as a mobile tooth fixing material, in terms of the flexibility and discharging force, the content of the (meth)acrylic block copolymer (A) is preferably 5 to 500 parts by mass and more preferably 10 to 250 parts by mass per 100 parts by mass of the total amount of the polymerizable monomer (B).

When the dental polymerizable composition of the present invention is used as a denture liner, in terms of the flexibility and discharging force, the content of the (meth)acrylic block copolymer (A) is preferably 10 to 1000 parts by mass and more preferably 20 to 500 parts by mass per 100 parts by mass of the total amount of the polymerizable monomer (B).

When the dental polymerizable composition of the present invention is used as a dental cement, in terms of the flexibility and discharging force, the content of the (meth)acrylic block copolymer (A) is preferably 2.0 to 500 parts by mass, more preferably 2.5 to 200 parts by mass, and even more preferably 5 to 100 parts by mass per 100 parts by mass of the total amount of the polymerizable monomer (B). When such a dental cement is used for temporary cementation, in terms of the flexibility and discharging force, the content of the (meth)acrylic block copolymer (A) is preferably 20 to 500 parts by mass and more preferably 40 to 400 parts by mass per 100 parts by mass of the total amount of the polymerizable monomer (B).

When the dental polymerizable composition of the present invention is used as a dental self-adhesive composite resin, in terms of the polymerization shrinkage stress and discharging force, the content of the (meth)acrylic block copolymer (A) is preferably 2.5 to 250 parts by mass and more preferably 5 to 100 parts by mass per 100 parts by mass of the total amount of the polymerizable monomer (B).

The dental polymerizable composition of the present invention may include a (meth)acrylic block copolymer other than the (meth)acrylic block copolymer (A) as long as the effects of the present invention are not impaired. The content of such an additional (meth)acrylic block copolymer is preferably less than 5.0 mass %, and more preferably less than 2.0 mass %.

The polymerization initiator (C) included in the dental polymerizable composition of the present invention is a photopolymerization initiator or a chemical polymerization initiator.

When the dental polymerizable composition of the present invention is used as a mobile tooth fixing material or a dental self-adhesive composite resin, the dental polymerizable composition preferably includes a photopolymerization initiator.

When the dental polymerizable composition of the present invention is used as a denture liner or a dental cement, the dental polymerizable composition preferably includes a chemical polymerization initiator.

Examples of the photopolymerization initiator include (bis)acylphosphine oxides, salts thereof, α-diketones, thioxanthones, quaternary ammonium salts of thioxanthones, ketals, coumarins, anthraquinones, benzoin alkyl ether compounds, and α-aminoketone compounds. In terms of the curability, (bis)acylphosphine oxides, salts thereof, and α-diketones are preferred.

Examples of the (bis)acylphosphine oxides that may be used as the photopolymerization initiator include: acylphosphine oxides such as 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoyldiphenylphosphine oxide, and benzoyl di-(2,6-dimethylphenyl)phosphonate; and bis acylphosphine oxides such as bis(2,6-dichlorobenzoyl)phenylphosphine oxide, bis(2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, bis(2,5,6-trimethylbenzoyl)-2,4,4-trimethylpentylphosphine oxide, 2,4,6-trimethylbenzoylphenylphosphine oxide sodium salt, 2,4,6-trimethylbenzoylphenylphosphine oxide potassium salt, and 2,4,6-trimethylbenzoylphenylphosphine oxide ammonium salt. Additional examples include compounds as disclosed in JP 2000-159621 A. Among these, particularly preferred are 2,4,6-trimethylbenzoyldiphenylphosphine oxide, 2,4,6-trimethylbenzoylmethoxyphenylphosphine oxide, bis-(2,4,6-trimethylbenzoyl)phenylphosphine oxide, and 2,4,6-trimethylbenzoylphenylphosphine oxide sodium salt.

Examples of the α-diketones that may be used as the photopolymerization initiator include diacetyl, dibenzyl, camphorquinone, 2,3-pentadione, 2,3-octadione, 9,10-phenanthrenequinone, 4,4'-oxybenzyl, and acenaphthenequinone. Among these, camphorquinone is particularly preferred in that it shows maximum absorption at a wavelength in the visible region.

When the dental polymerizable composition of the present invention includes a photopolymerization initiator, the partial structure (1) exhibits polymerizability upon irradiation with light, causing curing of the dental polymerizable composition of the present invention to form a cured product. The light as used herein refers to visible light, far-ultraviolet light, ultraviolet light (UV), near-ultraviolet light, infrared light, or the like. In terms of the safety for living bodies, cure rate, availability of an irradiation device, cost, etc., visible light is preferred.

Examples of the chemical polymerization initiator include organic peroxides such as ketone peroxides, hydroperoxides, diacyl peroxides, dialkyl peroxides, peroxyketals, peroxyesters, and peroxydicarbonates.

Examples of the ketone peroxides that may be used as the chemical polymerization initiator include methyl ethyl ketone peroxide, methyl isobutyl ketone peroxide, methyl cyclohexanone peroxide, and cyclohexanone peroxide.

Examples of the hydroperoxides that may be used as the chemical polymerization initiator include 2,5-dimethylhexane-2,5-dihydroperoxide, diisopropylbenzene hydroperoxide, cumene hydroperoxide, t-butyl hydroperoxide, and 1,1,3,3-tetramethylbutyl hydroperoxide.

Examples of the diacyl peroxides that may be used as the chemical polymerization initiator include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the diacyl peroxides that may be used as the chemical polymerization initiator include acetyl peroxide, isobutyryl peroxide, benzoyl peroxide, decanoyl peroxide, 3,5,5-trimethylhexanoyl peroxide, 2,4-dichlorobenzoyl peroxide, and lauroyl peroxide.

Examples of the peroxyketals that may be used as the chemical polymerization initiator include 1,1-bis(t-butylperoxy)-3,3,5-trimethylcyclohexane, 1,1-bis(t-butylperoxy)cyclohexane, 2,2-bis(t-butylperoxy)butane, 2,2-bis(t-butylperoxy)octane, and n-butyl 4,4-bis(t-butylperoxy)valerate.

Examples of the peroxyesters that may be used as the chemical polymerization initiator include α-cumyl peroxyneodecanoate, t-butyl peroxyneodecanoate, t-butyl peroxypivalate, 2,2,4-trimethylpentyl peroxy-2-ethylhexanoate, t-amyl peroxy-2-ethylhexanoate, t-butyl peroxy-2-ethylhexanoate, di-t-butyl peroxyisophthalate, di-t-butyl peroxyhexahydroterephthalate, t-butyl peroxy-3,3,5-trimethylhexanoate, t-butyl peroxyacetate, and t-butyl peroxybenzoate.

Examples of the peroxydicarbonates that may be used as the chemical polymerization initiator include di-3-methoxy peroxydicarbonate, di-2-ethylhexyl peroxydicarbonate, bis(4-t-butylcyclohexyl) peroxydicarbonate, diisopropyl peroxydicarbonate, di-n-propyl peroxydicarbonate, di-2-ethoxyethyl peroxydicarbonate, and diallyl peroxydicarbonate.

Among these organic peroxides, preferred are hydroperoxides in view of the overall balance of safety, storage stability, and polymerization initiation ability, and more preferred are cumene hydroperoxide, t-butyl hydroperoxide, and 1,1,3,3-tetramethylbutyl hydroperoxide.

The content of the polymerization initiator (C) is preferably 0.01 to 15 mass %, and more preferably 0.05 to 8 mass % with respect to the total dental polymerizable composition of the present invention.

In terms of the curability of the resulting composition, the content of the polymerization initiator (C) is preferably 0.001 to 30 parts by mass, more preferably 0.05 to 20 parts by mass, and even more preferably 0.1 to 10 parts by mass per 100 parts by mass of the total amount of the polymerizable monomer (B). When the content of the polymerization initiator (C) is less than 0.001 parts by mass, the polymerization may fail to progress sufficiently. When the content of the polymerization initiator (C) is more than 30 parts by mass, the initiator may be segregated from the composition.

Preferably, the dental polymerizable composition of the present invention includes a polymerization accelerator (D). Examples of the polymerization accelerator (D) include amines, sulfinic acids, sulfinates, sulfites, hydrogen sulfites, aldehydes, thiourea compounds, organophosphorus compounds, vanadium compounds, copper compounds, borate compounds, barbituric acid derivatives, triazine compounds, tin compounds, halogen compounds, and thiol compounds.

Examples of the amines that may be used as the polymerization accelerator (D) include: primary aliphatic amines such as n-butylamine, n-hexylamine, and n-octylamine; secondary aliphatic amines such as diisopropylamine, dibutylamine, and N-methylethanolamine; tertiary aliphatic amines such as N-methyldiethanolamine, N-ethyldiethanolamine, N-n-butyldiethanolamine, N-dodecyldiethanolamine, 2-(dimethylamino)ethyl methacrylate, N-methyldiethanolamine dimethacrylate, N-ethyldiethanolamine dimethacrylate, triethanolamine monomethacrylate, triethanolamine dimethacrylate, triethanolamine trimethacrylate, triethanolamine, trimethylamine, triethylamine, and tributylamine; and aromatic amines such as N,N-bis(2-hydroxyethyl)-3,5-dimethylaniline, N,N-di(2-hydroxyethyl)-p-toluidine, N,N-bis(2-hydroxyethyl)-3,4-dimethylaniline, N,N-bis(2-hydroxyethyl)-4-ethylaniline, N,N-bis(2-hydroxyethyl)-4-isopropylaniline, N,N-bis(2-hydroxyethyl)-4-t-butylaniline, N,N-bis(2-hydroxyethyl)-3,5-di-isopropylaniline, N,N-bis(2-hydroxyethyl)-3,5-di-t-butylaniline, N,N-dimethylaniline, N,N-dimethyl-p-toluidine, N,N-dimethyl-m-toluidine, N,N-diethyl-p-toluidine, N,N-dimethyl-3,5-dimethylaniline, N,N-dimethyl-3,4-dimethylaniline, N,N-dimethyl-4-ethylaniline, N,N-dimethyl-4-isopropylaniline, N,N-dimethyl-4-t-butylaniline, N,N-dimethyl-3,5-di-t-butylaniline, ethyl 4-(N,N-dimethylamino)benzoate, methyl 4-(N,N-dimethylamino)benzoate, n-butoxyethyl N,N-dimethylaminobenzoate, 2-(methacryloyloxy)ethyl 4-N,N-dimethylaminobenzoate, 4-N,N-dimethylaminobenzophenone, and butyl 4-(dimethylamino)benzoate. Among these, preferred are tertiary aliphatic amines in terms of the cure rate, more preferred are N-methyldiethanolamine, triethanolamine, N,N-di(2-hydroxyethyl)-p-toluidine, ethyl 4-(N,N-dimethylamino)benzoate, n-butoxyethyl N,N-dimethylaminobenzoate, and 4-N,N-dimethylaminobenzophenone, and even more preferred are N-methyldiethanolamine and triethanolamine in terms of storage stability.

Examples of the sulfinic acids and sulfinates that may be used as the polymerization accelerator (D) include p-toluenesulfinic acid, sodium p-toluenesulfinate, potassium p-toluenesulfinate, lithium p-toluenesulfinate, calcium p-toluenesulfinate, benzenesulfinic acid, sodium benzenesulfinate, potassium benzenesulfinate, lithium benzenesulfinate, calcium benzenesulfinate, 2,4,6-trimethylbenzenesulfinic acid, sodium 2,4,6-trimethylbenzenesulfinate, potassium 2,4,6-trimethylbenzenesulfinate, lithium 2,4,6-trimethylbenzenesulfinate, calcium 2,4,6-trimethylbenzenesulfinate, 2,4,6-triethylbenzenesulfinic acid, sodium 2,4,6-triethylbenzenesulfinate, potassium 2,4,6-triethylbenzenesulfinate, lithium 2,4,6-triethylbenzenesulfinate, calcium 2,4,6-triethylbenzenesulfinate, 2,4,6-triisopropylbenzenesulfinic acid, sodium 2,4,6-triisopropylbenzenesulfinate, potassium 2,4,6-triisopropylbenzenesulfinate, lithium 2,4,6-triisopropylbenzenesulfinate, and calcium 2,4,6-triisopropylbenzenesulfinate. Among these, sodium benzenesulfinate, sodium p-toluenesulfinate, and sodium 2,4,6-triisopropylbenzenesulfinate are preferred.

Examples of the sulfites and hydrogen sulfites that may be used as the polymerization accelerator (D) include sodium sulfite, potassium sulfite, calcium sulfite, ammonium sulfite, sodium hydrogen sulfite, and potassium hydrogen sulfite. Among these, sodium sulfite is preferred in terms of curability.

Examples of the aldehydes that may be used as the polymerization accelerator (D) include terephthalaldehydes; and benzaldehyde derivatives such as dimethylaminobenzaldehyde, p-methyloxybenzaldehyde, p-ethyloxybenzaldehyde, and p-n-octyloxybenzaldehyde. Among these, p-n-octyloxybenzaldehyde is preferred in terms of curability.

Examples of the thiourea compounds that may be used as the polymerization accelerator (D) include 1-(2-pyridyl)-2-thiourea, thiourea, methylthiourea, ethylthiourea, N,N'-dimethylthiourea, N,N'-diethylthiourea, N,N'-di-n-propylthiourea, N,N'-dicyclohexylthiourea, trimethylthiourea, triethylthiourea, tri-n-propylthiourea, tricyclohexylthiourea, tetramethylthiourea, tetraethylthiourea, tetra-n-propylthiourea, tetracyclohexylthiourea, 3,3-dimethylethylenethiourea, and 4,4-dimethyl-2-imidazolinethione. Among these, 1-(2-pyridyl)-2-thiourea or 4,4-dimethyl-2-imidazolinethione is preferred in terms of curability.

Examples of the organophosphorus compounds that may be used as the polymerization accelerator (D) include triphenylphosphine, 2-methyltriphenylphosphine, 4-methyltriphenylphosphine, 2-methoxytriphenylphosphine, 4-methoxytriphenylphosphine, tri-n-butylphosphine, tri-isobutylphosphine, and tri-t-butylphosphine. Among these, triphenylphosphine and 2-methyltriphenylphosphine are preferred in terms of curability.

Tetravalent and/or pentavalent vanadium compounds are preferred as the vanadium compounds that may be used as the polymerization accelerator (D). Examples of the tetravalent and/or pentavalent vanadium compounds include vanadium(IV) oxide, vanadyl(IV) acetylacetonate, vanadyl(IV) oxalate, vanadyl(IV) sulfate, oxobis(1-phenyl-1,3-butanedionato)vanadium(IV), bis(maltolato)oxovanadium(IV), vanadium(V) oxide, sodium metavanadate(V), and ammonium metavanadate(V).

Examples of the copper compounds that may be used as the polymerization accelerator (D) include copper acetylacetonate, copper(II) acetate, copper oleate, copper(II) chloride, and copper(II) bromide.

The content of the polymerization accelerator (D) is preferably 0.01 to 15 mass %, and more preferably 0.05 to 8 mass % with respect to the total dental polymerizable composition of the present invention.

In terms of, for example, the curability of the resulting composition, the content of the polymerization accelerator (D) is preferably 0.001 to 30 parts by mass, more preferably 0.05 to 20 parts by mass, and even more preferably 0.1 to 10 parts by mass per 100 parts by mass of the total amount of the polymerizable monomer (B). When the content of the polymerization accelerator (D) is less than 0.001 parts by mass, the polymerization may fail to progress sufficiently. When the content of the polymerization accelerator (D) is more than 30 parts by mass, the polymerization accelerator may be segregated from the composition.

The present invention may employ a combination of the chemical polymerization initiator and the polymerization accelerator (D) to form a redox polymerization initiator. In this case, it is preferable to store the chemical polymerization initiator and the polymerization accelerator (D) in separate containers, respectively, in consideration of storage stability, and to mix them just before use. Therefore, the dental polymerizable composition is preferably in a two-component form composed of a first component containing the chemical polymerization initiator and a second component containing the polymerization accelerator (D). More preferably, these first and second components are both in a paste form.

The dental polymerizable composition of the present invention may further include a filler (E) to adjust the discharging force or improve the mechanical strength of the resulting cured product. Examples of such a filler (E) include an organic filler, an inorganic filler, and an organic-inorganic composite filler.

Examples of the organic filler include polymethyl methacrylate, polyethyl methacrylate, methyl methacrylate-ethyl methacrylate copolymer, cross-linked polymethyl methacrylate, cross-linked polyethyl methacrylate, polyester, polyamide, polycarbonate, polyphenylene ether, polyoxymethylene, polyvinyl chloride, polystyrene, polyethylene, polypropylene, chloroprene rubber, nitrile rubber, ethylene-vinyl acetate copolymer, styrene-butadiene copolymer, acrylonitrile-styrene copolymer, and acrylonitrile-styrene-butadiene copolymer. These may be used alone or in combination with one another. The shape of the organic filler is not particularly limited, and the particle diameter of the filler can be selected for use as appropriate.

Examples of the inorganic filler include quartz, silica, alumina, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may be used alone or in combination with one other. The shape of the inorganic filler is not particularly limited. For example, an irregularly-shaped filler or a spherical filler can be selected for use as appropriate.

The above inorganic filler may optionally be surface-treated with a commonly-known surface treatment agent such as a silane coupling agent before use in order to adjust the miscibility with the polymerizable monomer (B). Examples of the surface treatment agent include vinyltrimethoxysilane, vinyltriethoxysilane, vinyltrichlorosilane, vinyl-tris(β-methoxyethoxy)silane, 3-methacryloyloxypropyltrimethoxysilane, 11-methacryloyloxyundecyltrimethoxysilane, 3-glycidoxypropyltrimethoxysilane, 3-mercaptopropyltrimethoxysilane, and 3-aminopropyltriethoxysilane.

The technique for the surface treatment is not particularly limited. Examples of the techniques include: a technique in which the above surface treatment agent is applied by spraying to the inorganic filler under vigorous stirring; a technique in which the inorganic filler and the above surface treatment agent are dispersed or dissolved in an appropriate solvent and then the solvent is removed; and a technique in which the alkoxy groups of the above surface treatment agent are hydrolyzed into silanol groups in an aqueous solution with the help of an acid catalyst so that the surface treatment agent is attached to the surface of the inorganic filler in the aqueous solution, and water is then removed. In any of these techniques, heating, usually at 50 to 150° C., can be used to fully complete the reaction between the surface of the inorganic filler and the surface treatment agent and thereby accomplish the surface treatment.

The organic-inorganic composite filler can be obtained, for example, by first adding a monomer compound to the above inorganic filler to form a paste, allowing the paste to undergo polymerization, and then grinding the resulting polymer. For example, a TMPT filler (filler obtained by mixing trimethylolpropane methacrylate and a silica filler, allowing the mixture to undergo polymerization, and then grinding the resulting polymer) can be used as the organic-inorganic composite filler. The shape of the organic-inorganic composite filler is not particularly limited, and the particle diameter of the filler can be selected for use as appropriate.

The average particle diameter of the filler (E) is preferably 0.001 to 50 μm and more preferably 0.001 to 10 μm in terms of, for example, the ease of handling of the resulting dental polymerizable composition and the mechanical strength of a cured product of the dental polymerizable composition. The average particle diameter of the filler as defined herein can be measured by any method known to persons skilled in the art and can be measured easily, for example, using a laser diffraction particle size distribution analyzer (SALD-2100, manufactured by Shimadzu Corporation) described in EXAMPLES below. The laser diffraction scattering method is convenient for particle diameter measurement of particles with a diameter of 0.1 μm or more, while the electron microscopic observation is convenient for particle diameter measurement of ultrafine particles with a diameter of 0.1 μm or less. 0.1 μm is the value measured by the laser diffraction scattering method.

To be more specific about the laser diffraction scattering method, the average particle diameter can be measured using a laser diffraction particle size distribution analyzer (SALD-2100, manufactured by Shimadzu Corporation) and using a 0.2% aqueous solution of sodium hexametaphosphate as a dispersion medium.

To be more specific about the electron microscopic observation, the average particle diameter can be measured by taking a photograph of the particles with a scanning electron microscope (S-4000, manufactured by Hitachi, Ltd.) and measuring the particle diameters of (200 or more) particles observed in a unit area of field of view in the photograph by the use of an image-analyzing particle size distribution analysis software (MacView manufactured by Mountech Co., Ltd.). In this case, the particle diameter of each particle is obtained as an arithmetic mean value of the longest and shortest dimensions thereof, and the average primary particle diameter is calculated from the number of the particles and their particle diameters.

In terms of the flexibility and discharging force, the content of the filler (E) in the dental polymerizable composition of the present invention is preferably 0 to 85 mass %, more preferably 0 to 80 mass %, and even more preferably 1 to 79 mass %.

When the dental polymerizable composition of the present invention is used as a mobile tooth fixing material or a denture liner, the content of the filler (E) in the dental polymerizable composition is preferably 0 to 70 mass %, more preferably 0 to 45 mass %, and even more preferably 0 to 18 mass %. When the dental polymerizable composition of the present invention is used as a mobile tooth fixing material or a denture liner, the composition preferably contains ultrafine particles having an average particle diameter of 0.1 μm or less as the filler (E).

When the dental polymerizable composition of the present invention is used as a dental cement, the content of the filler (E) in the dental polymerizable composition is preferably 0 to 80 mass %, more preferably 0 to 75 mass %, and even more preferably 20 to 70 mass %. When the dental polymerizable composition of the present invention is used as a dental cement, the composition preferably contains a filler having an average particle diameter of more than 1 μm as the filler (E).

When the dental polymerizable composition of the present invention is a dental self-adhesive composite resin, the content of the filler (E) in the dental polymerizable composition is preferably 15 to 85 mass %, more preferably 35 to 80 mass %, and even more preferably 46 to 79 mass %. When the dental polymerizable composition of the present invention is used as a dental self-adhesive composite resin, the composition preferably contains a filler having an average particle diameter of more than 1 μm as the filler (E).

When the dental polymerizable composition of the present invention is a mobile tooth fixing material or a denture liner, the content of the filler (E) is preferably 0 to 250 parts by mass and more preferably 0 to 100 parts by mass per 100 parts by mass of the total amount of the polymerizable components (the (meth)acrylic block copolymer (A) and the polymerizable monomer (B)), in terms of the ease of handling of the resulting dental polymerizable composition and the mechanical strength of a cured product of the composition.

When the dental polymerizable composition of the present invention is a dental cement, the content of the filler (E) is preferably 0 to 400 parts by mass and more preferably 0 to 300 parts by mass per 100 parts by mass of the total amount of the polymerizable components (the (meth)acrylic block copolymer (A) and the polymerizable monomer (B)).

When the dental polymerizable composition of the present invention is a dental self-adhesive composite resin, the content of the filler (E) is preferably 50 to 500 parts by mass and more preferably 100 to 400 parts by mass per 100 parts by mass of the total amount of the polymerizable components (the (meth)acrylic block copolymer (A) and the polymerizable monomer (B)).

Another polymer may be added to the dental polymerizable composition of the present invention for the purpose of modifying the properties such as flexibility and discharging properties as long as it does not depart from the gist of the present invention. Examples of the other polymer that may be added include natural rubber, synthetic polyisoprene rubber, liquid polyisoprene rubber and a hydrogenated product thereof, polybutadiene rubber, liquid polybutadiene rubber and a hydrogenated product thereof, styrene-butadiene rubber, chloroprene rubber, ethylene-propylene rubber, acrylic rubber, isoprene-isobutylene rubber, acrylonitrile-butadiene rubber, styrene elastomers (such as polystyrene-polyisoprene-polystyrene block copolymer, polystyrene-polybutadiene-polystyrene block copolymer, poly(α-methylstyrene)-polybutadiene-poly(α-methylstyrene) block copolymer, poly(p-methylstyrene)-polybutadiene-poly(p-methylstyrene) block copolymer, and their hydrogenated products), and poly(methacrylic acid ester)-poly(acrylic acid ester)-poly(methacrylic acid ester) block copolymer having no curable functional group.

The dental polymerizable composition of the present invention may include a softener where necessary. Examples of the softener include: petroleum-derived softeners such as paraffinic, naphthenic, and aromatic process oils; paraffin; and vegetable oil-derived softeners such as peanut oil and rosin. These softeners may be used alone or in combination with one another. The content of the softener is not particularly limited as long as it does not depart from the gist of the present invention. The content is typically 300 parts by mass or less and preferably 100 parts by mass or less per 100 parts by mass of the total amount of the (meth)acrylic block copolymer (A) and the polymerizable monomer (B).

Furthermore, the dental polymerizable composition of the present invention may include a commonly-known additive to the extent that the additive causes no degradation in the performance of the composition. Examples of the additive include a polymerization inhibitor, an antioxidant, a pigment, a dye, an ultraviolet absorber, and a thickener.

Examples of the polymerization inhibitor include hydroquinone, hydroquinone monomethyl ether, dibutylhydroquinone, dibutylhydroquinone monomethyl ether, t-butylcatechol, 2-t-butyl-4,6-dimethylphenol, 2,6-di-t-butylphenol, and 3,5-di-t-butyl-4-hydroxytoluene. The content of the polymerization inhibitor is preferably 0.001 to 1.0 parts by mass per 100 parts by mass of the total amount of the polymerizable components (the (meth)acrylic block copolymer (A) and the polymerizable monomer (B)).

The dental polymerizable composition of the present invention requires less discharging force and is easily formable. The dental polymerizable composition of the present invention also has flexibility and thus high shock absorbing capacity after being cured, has low polymerization shrinkage stress during curing and thus good adhesion, and has high surface gloss and stain resistance. The dental polymerizable composition of the present invention is thus best suited for use as a mobile tooth fixing material, a denture liner, and a dental cement, and is suitable also for use as a dental self-adhesive composite resin due to its capability of reducing polymerization shrinkage stress.

An example of the preferred constitution of the mobile tooth fixing material is shown below. It is preferable for the mobile tooth fixing material to contain 5 to 500 parts by mass of the (meth)acrylic block copolymer (A), 0.05 to 20 parts by mass of the polymerization initiator (C), and 0.05 to 20 parts by mass of the polymerization accelerator (D) per 100 parts by mass of the total amount of the polymerizable monomer (B) and contain 0 to 250 parts by mass of the filler (E) per 100 parts by mass of the total amount of the polymerizable components (the (meth)acrylic block copolymer (A) and the polymerizable monomer (B)). It is more preferable for the mobile tooth fixing material to contain 10 to 250 parts by mass of the (meth)acrylic block copolymer (A), 0.1 to 10 parts by mass of the polymerization initiator (C), and 0.1 to 10 parts by mass of the polymerization accelerator (D) per 100 parts by mass of the polymerizable monomer (B) and contain 0 to 100 parts by mass of the filler (E) per 100 parts by mass of the total amount of the polymerizable components (the (meth)acrylic block copolymer (A) and the polymerizable monomer (B)).

An example of the preferred constitution of the denture liner is shown below. It is preferable for the denture liner to include 10 to 1000 parts by mass of the (meth)acrylic block copolymer (A), 0.05 to 20 parts by mass of the polymerization initiator (C), and 0.05 to 20 parts by mass of the polymerization accelerator (D) per 100 parts by mass of the total amount of the polymerizable monomer (B) and contain 0 to 250 parts by mass of the filler (E) per 100 parts by mass of the total amount of the polymerizable components (the (meth)acrylic block copolymer (A) and the polymerizable monomer (B)). It is more preferable for the denture liner to contain 20 to 500 parts by mass of the (meth)acrylic block copolymer (A), 0.1 to 10 parts by mass of the polymerization initiator (C), and 0.1 to 10 parts by mass of the polymerization accelerator (D) per 100 parts by mass of the polymerizable monomer (B) and contain 0 to 100 parts by mass of the filler (E) per 100 parts by mass of the total amount of the polymerizable components (the (meth)acrylic block copolymer (A) and the polymerizable monomer (B)).

An example of the preferred constitution of the dental cement is shown below. It is preferable for the dental cement to contain 5 to 500 parts by mass of the (meth)acrylic block copolymer (A), 0.05 to 20 parts by mass of the polymerization initiator (C), and 0.05 to 20 parts by mass of the polymerization accelerator (D) per 100 parts by mass of the total amount of the polymerizable monomer (B) and contain 0 to 400 parts by mass of the filler (E) per 100 parts by mass of the total amount of the polymerizable components (the (meth)acrylic block copolymer (A) and the polymerizable monomer (B)). It is more preferable for the dental cement to contain 20 to 400 parts by mass of the (meth)acrylic block copolymer (A), 0.1 to 10 parts by mass of the polymerization initiator (C), and 0.1 to 10 parts by mass of the polymerization accelerator (D) per 100 parts by mass of the polymerizable monomer (B) and contain 0 to 300 parts by mass of the filler (E) per 100 parts by mass of the total amount of the polymerizable components (the (meth)acrylic block copolymer (A) and the polymerizable monomer (B)).

An example of the preferred constitution of the dental self-adhesive composite resin is shown below. It is preferable for the dental self-adhesive composite resin to contain 2.5 to 250 parts by mass of the (meth)acrylic block copolymer (A), 0.05 to 20 parts by mass of the polymerization initiator (C), and 0.05 to 20 parts by mass of the polymerization accelerator (D) per 100 parts by mass of the total amount of the polymerizable monomer (B) and contain 50 to 500 parts by mass of the filler (E) per 100 parts by mass of the total amount of the polymerizable components (the (meth)acrylic block copolymer (A) and the polymerizable monomer (B)). It is more preferable for the dental self-adhesive composite resin to contain 5 to 100 parts by mass of the (meth)acrylic block copolymer (A), 0.1 to 10 parts by mass of the polymerization initiator (C), and 0.1 to 10 parts by mass of the polymerization accelerator (D) per 100 parts by mass of the polymerizable monomer (B) and contain 100 to 400 parts by mass of the filler (E) per 100 parts by mass of the total amount of the polymerizable components (the (meth)acrylic block copolymer (A) and the polymerizable monomer (B)).

The conditions of the mobile tooth fixing material, denture liner, dental cement, and dental self-adhesive composite resin of the preferred embodiments, such as the types of the components and the contents thereof, can be selected or changed as appropriate within the ranges separately described herein.

The light used to cure the dental polymerizable composition of the present invention is preferably visible light. An LED, a halogen lamp, an arc light, a xenon lamp, or a combination thereof may be used for irradiation of visible light.

Any conventional method for preparing a dental polymerizable composition can be used to prepare the dental polymerizable composition of the present invention. For example, a method for mixing the components in predetermined proportions to obtain a homogeneous mixture can be used. The homogeneous mixture obtained by mixing the components may be degassed under vacuum.

EXAMPLES

The present invention will now be described specifically with reference to examples and comparative examples. It should be noted that the present invention is not limited to these examples.

In the following examples and comparative examples, the raw materials were dried and purified in a conventional manner and degassed with nitrogen before use. The raw materials thus prepared were transferred and added in a nitrogen atmosphere.

[Monomer Consumption Rate]

0.5 ml of a polymerization reaction solution was removed and added to 0.5 ml of methanol to mix them. 0.1 ml of the mixture solution thus obtained was removed and dissolved in 0.5 ml of deuterated chloroform. The resulting mixture was subjected to $^1$H-NMR (using ECX400 manufactured by JEOL, measurement temperature=25° C.). The result was analyzed to calculate the monomer consumption rates of monomers consumed for polymerization.

[Mn and Molecular Weight Distribution]

A polymer obtained was analyzed by gel permeation chromatography (system: HLC-8020GPC manufactured by Tosoh Corporation, column: TSK-gel SuperMultipore HZ-M (column diameter=4.6 mm, column length=15 cm) manufactured by Tosoh Corporation, measurement conditions: flow rate=0.35 ml/min, temperature=40° C., eluent=tetrahydrofuran) to calculate the Mn on a polystyrene-equivalent basis and the molecular weight distribution (Mw/Mn) of the polymer.

[Polymerization Initiation Efficiency]

The polymerization initiation efficiency (F1) in the step (I) is calculated from the following equation:

$$F1(\%)=100 \times Mn(I-1)/Mn(R-1),$$

where Mn(R-1) is the Mn of the polymer actually obtained in the step [I] and Mn(I-1) is the Mn (calculated value) of the polymer theoretically obtained in the step [I] with a polymerization initiation efficiency of 100%.

[Blocking Efficiency]

The blocking efficiency (F2) during a period from the end of the step [I] to the end of the step [II] is calculated from the following equation:

$$F2(\%)=10000 \cdot \{Mn(I-2)-Mn(I-1)\}/[F1 \cdot \{Mn(R-2)-Mn(R-1)\}],$$

where Mn(R-2) is the Mn of the block copolymer (A) actually obtained in the step [II] and Mn(I-2) is the Mn (calculated value) of the block copolymer (A) theoretically obtained in the step [II] with a blocking efficiency of 100%.

Synthesis Example 1

(Step [I])

The inside of a 3-liter flask was dried and purged with nitrogen, and 1.5 liters of toluene was added to the flask. While stirring the solution in the flask, 7.4 ml (27.3 mmol) of 1,1,4,7,10,10-hexamethyltriethylenetetramine as a Lewis base and 63.6 ml (28.6 mmol) of a 0.450 mol/L toluene solution of isobutylbis(2,6-di-t-butyl-4-methylphenoxy)aluminum as an organoaluminum compound were sequentially added to the flask. Then, the resulting mixture was cooled to −20° C. 20 ml (26.0 mmol) of a 1.30 mol/L cyclohexane solution of sec-butyllithium as an organolithium compound was further added to the flask, and then 35. 3 ml of a mixture of monomers, i.e., 18.7 ml (78 mmol) of 1,1-dimethylpropane-1,3-diol dimethacrylate and 16.6 ml (156 mmol) of methyl methacrylate, was added at once. Anionic polymerization was thus initiated. After the completion of the addition of the mixture, the polymerization reaction solution turned from original yellow to colorless in 80 minutes. The reaction solution was stirred for another 20 minutes, and a portion of the reaction solution was sampled. In the step [I], the consumption rate of 1,1-dimethylpropane-1,3-diol dimethacrylate and that of methyl methacrylate were 100%. The Mn (Mn(R-1)) of the obtained polymer was 1,340, and the Mw/Mn thereof was 1.16. Further, the polymerization initiation efficiency (F1) in the step [I] was 99%.

(Step [II])

Subsequently, while stirring the reaction solution at −20° C., 31.8 ml (14.3 mmol) of a 0.450 mol/L toluene solution of isobutylbis(2,6-di-t-butyl-4-methylphenoxy)aluminum as an organoaluminum compound was added, and after 1 minute, 504 ml (3.5 mol) of n-butyl acrylate as a monomer was added at a rate of 10 ml/min. A portion of the reaction solution was sampled immediately after the completion of the addition of n-butyl acrylate. In the step [II], the consumption rate of n-butyl acrylate was 100%. The Mn (Mn (R-2)) of the obtained polymer was 21,300, and the Mw/Mn thereof was 1.18. Further, the blocking efficiency (F2) from the end of the step [I] throughout the step [II] was 100%.

(Step [III])

Subsequently, while stirring the reaction solution at −20° C., 30.7 ml of a mixture of monomers, i.e., 16.3 ml (67.8 mmol) of 1,1-dimethylpropane-1,3-diol dimethacrylate and 14.4 ml (136 mmol) of methyl methacrylate, was added at once. Then, the temperature of the resulting mixture was raised to 20° C. at a rate of 2° C./min. A portion of the reaction solution was sampled 60 minutes after the completion of the addition of the mixture of monomers. In the step [III], the consumption rate of 1,1-dimethylpropane-1,3-diol dimethacrylate and that of methyl methacrylate were 100%.

(Step [IV])

Subsequently, while stirring the reaction solution at 20° C., 100 ml of methanol was added to terminate the anionic polymerization. The resultant solution was poured into 10 liters of methanol, and the polymer was precipitated and collected by filtration, followed by drying at 100° C. and 30 Pa. Thus, 471 g of (meth)acrylic block copolymer (A) (hereinafter referred to as a "(meth)acrylic block copolymer (A-1)") was obtained. The Mn of the obtained (meth)acrylic block copolymer (A-1) was 22,600, and the Mw/Mn thereof was 1.19.

Synthesis Example 2

(Step [I])

The inside of a 3 liter-flask was dried and purged with nitrogen, and 1.5 liters of toluene was added to the flask. While stirring the solution in the flask, 1.5 ml (5.5 mmol) of 1,1,4,7,10,10-hexamethyltriethylenetetramine as a Lewis base and 12.7 ml (5.7 mmol) of a 0.450 mol/L toluene solution of isobutylbis(2,6-di-t-butyl-4-methylphenoxy)aluminum as an organoaluminum compound were sequentially added to the flask. Then, the resulting mixture was cooled to −20° C. 4.0 ml (5.2 mmol) of a 1.30 mol/L cyclohexane solution of sec-butyllithium as an organolithium compound was further added to the flask, and then 35.7 ml of a mixture of monomers, i.e., 37.4 ml (156 mmol) of 1,1-dimethylpropane-1,3-diol dimethacrylate and 8.3 ml (78 mmol) of methyl methacrylate, was added at once. Anionic polymerization was thus initiated. After the completion of the addition of the mixture, the polymerization reaction solution turned from original yellow to colorless in 80 minutes. The reaction solution was stirred for another 20 minutes, and a portion of the reaction solution was sampled. In the step [I], the consumption rate of 1,1-dimethylpropane-1,3-diol dimethacrylate and that of methyl methacrylate were 100%. The Mn (Mn(R-1)) of the obtained polymer was 7,860, and the Mw/Mn thereof was 1.23. Further, the polymerization initiation efficiency (F1) in the step [I] was 99%.

(Step [II])

Subsequently, while stirring the reaction solution at −20° C., 6.4 ml (2.9 mmol) of a 0.450 mol/L toluene solution of isobutylbis(2,6-di-t-butyl-4-methylphenoxy)aluminum as an organoaluminum compound was added, and after 1 minute, 300 ml (2.1 mol) of n-butyl acrylate as a monomer was added at a rate of 10 ml/min. A portion of the reaction solution was sampled immediately after the completion of the addition of n-butyl acrylate. In the step [II], the consumption rate of n-butyl acrylate was 100%. The Mn (Mn(R-2)) of the obtained polymer was 72,500, and the Mw/Mn thereof was 1.20. Further, the blocking efficiency (F2) from the end of the step [I] throughout the step [II] was 100%.

(Step [III])

Subsequently, while stirring the reaction solution at −20° C., 35.7 ml of a mixture of monomers, i.e., 37.4 ml (156 mmol) of 1,1-dimethylpropane-1,3-diol dimethacrylate and 8.3 ml (78 mmol) of methyl methacrylate, was added at once. Then, the temperature of the resulting mixture was raised to 20° C. at a rate of 2° C./min. A portion of the reaction solution was sampled 60 minutes after the completion of the addition of the mixture of monomers. In the step [III], the consumption rate of 1,1-dimethylpropane-1,3-diol dimethacrylate and that of methyl methacrylate were 100%.

(Step [IV])

Subsequently, while stirring the reaction solution at 20° C., 100 ml of methanol was added to terminate the anionic polymerization. The resultant solution was poured into 10 liters of methanol, and the polymer was precipitated and collected by filtration, followed by drying at 100° C. and 30 Pa. Thus, 280 g of (meth)acrylic block copolymer (A) (hereinafter referred to as a "(meth)acrylic block copolymer (A-2)") was obtained. The Mn of the obtained (meth)acrylic block copolymer (A-2) was 80,000, and the Mw/Mn thereof was 1.21.

Synthesis Example 3

(Step [I])

The inside of a 3-liter flask was dried and purged with nitrogen, and 1.5 liters of toluene was added to the flask. While stirring the solution in the flask, 7.4 ml (27.3 mmol) of 1,1,4,7,10,10-hexamethyltriethylenetetramine as a Lewis base and 63.6 ml (28.6 mmol) of a 0.450 mol/L toluene solution of isobutylbis(2,6-di-t-butyl-4-methylphenoxy)aluminum as an organoaluminum compound were sequentially added to the flask. Then, the resulting mixture was cooled to −20° C. 20 ml (26.0 mmol) of a 1.30 mol/L cyclohexane solution of sec-butyllithium as an organolithium compound was further added to the flask, and then 35.3 ml of a mixture of monomers, i.e., 18.7 ml (78 mmol) of 1,1-dimethylpropane-1,3-diol dimethacrylate and 16.6 ml (103 mmol) of t-butyl methacrylate, was added at once. Anionic polymerization was thus initiated. After the completion of the addition of the mixture, the polymerization reaction solution turned from original yellow to colorless in 80 minutes. The reaction solution was stirred for another 20 minutes, and a portion of the reaction solution was sampled. In the step [I], the consumption rate of 1,1-dimethylpropane-1,3-diol dimethacrylate and that of t-butyl methacrylate were 100%. The Mn (Mn(R-1)) of the obtained polymer was 1,250, and the Mw/Mn thereof was 1.18. Further, the blocking efficiency (F1) in the step [I] was 99%.

(Step [II])

Subsequently, while stirring the reaction solution at −20° C., 31.8 ml (14.3 mmol) of a 0.450 mol/L toluene solution of isobutylbis(2,6-di-t-butyl-4-methylphenoxy)aluminum as an organoaluminum compound was added, and after 1 minute, 504 ml (2.4 mol) of 2-ethylhexyl acrylate as a monomer was added at a rate of 10 ml/min. A portion of the reaction solution was sampled immediately after the completion of the addition of 2-ethylhexyl acrylate. In the step [II], the consumption rate of 2-ethylhexyl acrylate was 100%. The Mn (Mn(R-2)) of the obtained polymer was 19,200, and the Mw/Mn thereof was 1.19. Further, the polymerization initiation efficiency (F2) from the end of the step [I] throughout the step [II] was 100%.

(Step [III])

Subsequently, while stirring the reaction solution at −20° C., 35.3 ml of a mixture of monomers, i.e., 18.7 ml (78 mmol) of 1,1-dimethylpropane-1,3-diol dimethacrylate and 16.6 ml (103 mmol) of t-butyl methacrylate, was added at once. Then, the temperature of the resulting mixture was raised to 20° C. at a rate of 2° C./min. A portion of the reaction solution was sampled 60 minutes after the completion of the addition of the mixture of monomers. In the step [III], the consumption rate of 1,1-dimethylpropane-1,3-diol dimethacrylate and that of t-butyl methacrylate were 100%.

(Step [IV])

Subsequently, while stirring the reaction solution at 20° C., 100 ml of methanol was added to terminate the anionic polymerization. The resultant solution was poured into 10 liters of methanol, and the polymer was precipitated and collected by filtration, followed by drying at 100° C. and 30 Pa. Thus, 450 g of (meth)acrylic block copolymer (A) (hereinafter referred to as a "(meth)acrylic block copolymer (A-3)") was obtained. The Mn of the obtained (meth)acrylic block copolymer (A-3) was 21,600, and the Mw/Mn thereof was 1.20.

Synthesis Example 4

(Step [I]')

The inside of a 1-liter three-neck flask was degassed and purged with nitrogen, and then 390 g of toluene, 1.4 ml of N,N',N',N'',N''-pentamethyldiethylenetriamine, and 18 ml of a toluene solution containing 11 mmol of isobutylbis(2,6-di-t-butyl-4-methylphenoxy)aluminum were added to the flask at room temperature, followed by addition of 1.7 ml of a cyclohexane/n-hexane mixture solution containing 2.2 mmol of sec-butyllithium. To the resulting solution was added 14 ml of methyl methacrylate, and the solution was allowed to react at room temperature for 1 hour. At this point of time, 1 g of the reaction solution was removed and prepared as a sample specimen 1. Subsequently, the reaction solution was cooled to an internal temperature of −15° C., and 120 ml of n-butyl acrylate was added dropwise to the solution over 6 hours. After the completion of dropping, 1 g of the reaction solution was removed and prepared as a sample specimen 2. Subsequently, 14 ml of methyl methacrylate was added, the temperature of the reaction solution was raised to room temperature, and the solution was stirred for about 10 hours. 1 g of methanol was added to the reaction solution to terminate the polymerization. After the termination of the polymerization, the reaction solution was poured into a large amount of liquid mixture of methanol and water (methanol: 90 mass %), and the resulting white precipitate produced was collected and prepared as a sample specimen 3.

Step [II]

The sample specimens 1 to 3 removed or collected in the above step [I]' were subjected to GPC measurement and $^1$H-NMR measurement in the manners described above. The Mw and Mw/Mn of a polymer or block copolymer obtained in each step of polymerization and the mass ratio between the methyl methacrylate polymer (PMMA) block and the n-butyl acrylate polymer (PnBA) block were calculated based on the results of the measurements. As a result, it was found that the white precipitate obtained in the step [I]' was a triblock copolymer represented by PMMA-PnBA-PMMA (hereinafter referred to as a "(meth)acrylic block copolymer 1") and that the Mw of the whole triblock copolymer was 85,000, the Mw/Mn thereof was 1.13, the mass ratio of these two polymer blocks was PMMA (10 mass %)—PnBA (80 mass %)—PMMA (10 mass %) (20 mass % of PMMA in total). The specimen 1 was PMMA, and the Mw and Mw/Mn thereof were 7,300 and 1.06, respectively. The specimen 2 was PMMA-PnBA diblock copolymer, and the Mw and Mw/Mn thereof were 77,000 and 1.16, respectively.

[Polymerizable Monomer (B)]
MDP: 10-methacryloyloxydecyl dihydrogen phosphate
3G: Triethylene glycol dimethacrylate
UDMA: 2,2,4-trimethylhexamethylenebis(2-carbamoyloxyethyl) dimethacrylate
DFHM: 1H,1H,7H-dodecafluoroheptyl methacrylate
BEM: 2-butoxyethyl methacrylate
D-2.6E: 2,2-bis(4-methacryloyloxypolyethoxyphenyl)propane (having an average number of moles of added ethoxy groups of 2.6)

[Photopolymerization Initiator (C-1)]
CQ: Camphorquinone
BAPO: Bis(2,4,6-trimethylbenzoyl)phenylphosphine oxide

[Chemical Polymerization Initiator (C-2)]
THP: 1,1,3,3-tetramethylbutyl hydroperoxide
CHP: Cumene hydroperoxide

[Polymerization Accelerator (D)]
PDE: Ethyl 4-(N,N-dimethylamino)benzoate
PTU: 1-(2-pyridyl)-2-thiourea
DMETU: 4,4-dimethyl-2-imidazolinethione
VOAA: Vanadyl(IV) acetylacetonate
CUA: Copper(II) acetate

[Filler (E)]
Filler (E)-1: Colloidal Silica Powder ("Aerosil 380" Manufactured by Nippon Aerosil Co., Ltd., Average Particle Diameter: 7 nm)
Filler (E)-2: 3-Methacryloyloxypropyltrimethoxysilane-Treated Silica Powder 100 g of silica powder obtained by grinding silica ("Aerosil 130" manufactured by Nippon Aerosil Co., Ltd.) in a vibratory ball mill, 0.5 g of 3-methacryloyloxypropyltrimethoxysilane, and 200 ml of toluene were put into a 500-ml eggplant-shaped flask, which was stirred at room temperature for 2 hours. Subsequently, toluene was distilled off under reduced pressure, residue of which was thereafter dried under vacuum at 40° C. for 16 hours, and further dried under vacuum at 90° C. for 3 hours. Thus, 3-methacryloyloxypropyltrimethoxysilane-treated silica powder (filler (E)-2) was obtained. The average particle diameter of the filler (E)-2 was measured using a laser diffraction particle size distribution analyzer (Model "SALD-2100" manufactured by Shimadzu Corporation) and using a 0.2% aqueous solution of sodium hexametaphosphate as a dispersion medium. As a result, the average particle diameter was 0.02 µm.

Filler (E)-3: 3-Methacryloyloxypropyltrimethoxysilane-Treated Barium Glass Powder 100 g of barium glass powder obtained by grinding barium glass ("E-3000" manufactured by Esstech, Inc.) in a vibratory ball mill, 0.5 g (0.5 parts by weight per 100 parts by weight of core filler material) of 3-methacryloyloxypropyltrimethoxysilane ("KBM-503" manufactured by Shin-Etsu Silicone, Co.), and 200 ml of toluene were put into a 500-ml eggplant-shaped flask, which was stirred at room temperature for 2 hours. Subsequently, toluene was distilled off under reduced pressure, residue of which was thereafter dried under vacuum at 40° C. for 16 hours, and further dried under vacuum at 90° C. for 3 hours. Thus, 3-methacryloyloxypropyltrimethoxysilane-treated barium glass powder (filler (E)-3) was obtained. The average particle diameter of the filler (E)-3 was measured using a laser diffraction particle size distribution analyzer (Model "SALD-2100" manufactured by Shimadzu Corporation) and using a 0.2% aqueous solution of sodium hexametaphosphate as a dispersion medium. As a result, the average particle diameter was 2.4 µm.

[Polymerization Inhibitor]
BHT: 3,5-di-t-butyl-4-hydroxytoluene

Dental polymerizable compositions according to Examples 1 to 6 and Comparative Examples 1 and 2, which were intended to be used as mobile tooth fixing materials, were prepared by mixing the components in proportions shown in Table 1 at 20° C.

Pastes A (corresponding to first components) and pastes B (corresponding to second components) for dental polymerizable compositions according to Examples 7 to 12 and Comparative Examples 3 and 4, which were intended to be used as denture liners, were prepared by mixing the components in proportions shown in Table 2 at 20° C.

Pastes A (corresponding to first components) and pastes B (corresponding to second components) for dental polymerizable compositions according to Examples 13 to 18 and Comparative Examples 5 and 6, which were intended to be used as dental cements, were prepared by mixing the components in proportions shown in Table 3 at 20° C.

Dental polymerizable compositions of Examples 19 to 24 and Comparative Examples 7 and 8, which were intended to be used as dental self-adhesive composite resins, were prepared by mixing the components in proportions shown in Table 4 at 20° C.

Test Example 1: Discharging Force

The dental polymerizable compositions for use as mobile tooth fixing materials prepared in Examples 1 to 6 and Comparative Examples 1 and 2 and the dental polymerizable compositions for use as dental self-adhesive composite resins prepared in Examples 19 to 24 and Comparative Examples 7 and 8 were each placed in a 1.5 ml-container for a commercially available dental composite resin (CLEARFIL MAJESTY LV manufactured by Kuraray Noritake Dental Inc.) fitted at the tip with a guide tip having an inner diameter of 0.5 mm. Next, a plunger was inserted into the container by lowering a crosshead fitted with a jig for compressive strength test in the container at a rate of 4 mm/min using an Autograph tester (AG-100kNI manufactured by Shimadzu Corporation), so as to apply a load to the polymerizable composition to discharge it through the guide tip. The maximum load applied was determined as the discharging force. The results are shown in Table 1 and Table 4.

The pastes A and pastes B for the dental polymerizable compositions for use as denture liners prepared in Examples 7 to 12 and Comparative Examples 3 and 4 and the pastes A and pastes B for the dental polymerizable compositions for use as dental cements prepared in Examples 13 to 18 and Comparative Examples 5 and 6 were each placed in two pockets of a 5 ml-container for a commercially available dental cement (CLEARFIL ESTHETIC CEMENT manufactured by Kuraray Noritake Dental Inc.) fitted at the tip with a mixing tip having an inner diameter of 0.8 mm. Next, a pair of plungers were inserted into the respective pockets of the container by lowering a crosshead fitted with a jig for compressive strength test in the container at a rate of 4 mm/min using an Autograph tester (AG-100kNI manufactured by Shimadzu Corporation), so as to mix the paste A and the paste B in the mixing tip, apply a load to the resulting mixture, and discharge it through the mixing tip. The maximum load applied was determined as the discharging force. The results are shown in Table 2 and Table 3.

When the discharging force required is 50 N or less, the paste can be discharged from the container easily with one hand, which means that the paste has superior discharging properties. When the discharging force required is more than 50 N and 80 N or less, the paste can be discharged but both hands may be required to discharge the paste. When the discharging force required is more than 80 N, it is difficult to discharge the paste even with both hands.

Test Example 2: Formability

A circle of 4 mm diameter was drawn on a dental mixing paper having a length of 59 mm and a width of 83 mm, and 0.3 g of each of the dental polymerizable compositions for use as mobile tooth fixing materials prepared in Examples 1 to 6 and Comparative Examples 1 and 2 and the dental polymerizable compositions for use as dental self-adhesive composite resins prepared in Examples 19 to 24 and Comparative Examples 7 and 8 was placed inside the circle to form a hemisphere covering the whole circle. This dental mixing paper was held in an upright position in a thermostat set at 37° C., and allowed to stand for 3 minutes, after which the length of the dental polymerizable composition moving down beyond the circle was measured. This test was repeated three times, and the average of the three measured values was determined as the flow distance (mm). A dental polymerizable composition with a longer flow distance is more runny. The results are shown in Table 1 and Table 4.

For each of the dental polymerizable compositions for use as denture liners prepared in Examples 7 to 12 and Comparative Examples 3 and 4 and the dental polymerizable compositions for use as dental cements prepared in Examples 13 to 18 and Comparative Examples 5 and 6, the flow distance was measured in the same manner as described above using a mixture of the paste A and the paste B as the dental polymerizable composition. The results are shown in Table 2 and Table 3.

A dental polymerization composition with a flow distance of 3 mm or more has no formability and thus has poor handling properties.

Test Example 3: Flexural Modulus

The dental polymerizable compositions for use as mobile tooth fixing materials prepared in Examples 1 to 6 and Comparative Examples 1 and 2 were each charged into a tubular mold (made of stainless steel and having dimensions of 2 mm (inner diameter)×2 mm (wall thickness)×25 mm (length)) placed on a glass slide, and another glass slide was placed on the mold. Next, each of the two surfaces of the dental polymerizable composition are irradiated with light through the glass slides using a dental visible light irradiation device (Pencure 2000 manufactured by Morita Corporation) at five points for 10 seconds per each point, and thus the composition was cured to obtain a test specimen.

For each of the dental polymerizable compositions for use as dental cements prepared in Examples 13 to 18 and Comparative Examples 5 and 6, a mixture of the paste A and the paste B as the dental polymerizable composition was charged in the same mold as mentioned above placed on a glass slide, and another glass slide was placed on the mold. The dental polymerizable composition in the mold was allowed to stand in a thermostat set at 37° C. for 30 minutes, and thus the composition was cured to obtain a test specimen. The test specimen thus obtained was subjected to a bending test using an Autograph tester (AG-100kNI manufactured by Shimadzu Corporation) at a crosshead speed of 1 mm/min so as to measure the flexural modulus of the test specimen. The results are shown in Table 1 and Table 3.

The flexural modulus is preferably in the range of 500 to 2000 MPa in terms of shock resistance.

Test Example 4: Type A Hardness

For each of the dental polymerizable compositions for use as denture liners prepared in Examples 7 to 12 and Comparative Examples 3 and 4, a mixture of the paste A and the paste B as the dental polymerizable composition was charged into a ring-shaped mold (made of stainless steel and having an inner diameter of 1.5 cm and a thickness of 2 mm) placed on a glass slide, and another glass slide was placed on the mold. Then, the composition in the mold was allowed to stand in a thermostat set at 37° C. for 30 minutes, and thus the composition was cured to obtain a disk-shaped test specimen. The hardness (type A hardness) of the test specimen thus obtained as a cured product was measured at 37° using a type A durometer according to JIS K 7215 and used as a measure of flexibility. The respective results are shown in Table 2.

The type A hardness at 37° C. is preferably 50 or less in terms of flexibility.

Test Example 5: Compression Set

A disk-shaped test specimen was obtained in the same manner as in Test Example 4 except that a ring-shaped mold (made of stainless steel and having an inner diameter of 1.5 cm and a thickness of 5 mm) was used instead of a ring-shaped mold (made of stainless steel and having an inner diameter of 1.5 cm and a thickness of 2 mm). The obtained test specimen was used to measure the compression set caused by exposure to conditions of a temperature of 37° C. and a compression deformation of 25% for 24 hours. The compression set was calculated by the following equation.

Compression set [%]={5−(thickness measured after test (mm))}/1.25×100 The respective results are shown in Table 2. The compression set at 37° C. is preferably 30% or less in terms of shape retention.

Test Example 6: Surface Gloss

The dental polymerizable compositions for use as mobile tooth fixing materials prepared in Examples 1 to 6 and Comparative Examples 1 and 2 and the dental polymerizable compositions for use as dental self-adhesive composite resins prepared in Examples 9 to 24 and Comparative Examples 7 and 8 were each charged into a ring-shaped mold (made of stainless steel and having an inner diameter of 20 mm and a thickness of 2 mm) placed on a glass slide, and another glass slide was placed on the mold. Next, each of the two surfaces of the dental polymerizable composition are irradiated with light through the glass slides using a dental visible light irradiation device (Pencure 2000 manufactured by Morita Corporation) at six points for 10 seconds per each point, and thus the composition was cured to obtain a test specimen.

For each of the dental polymerizable compositions for use as denture liners prepared in Examples 7 to 12 and Comparative Examples 3 and 4 and the dental polymerizable compositions for use as dental cements prepared in Examples 13 to 18 and Comparative Examples 5 and 6, a mixture of the paste A and the paste B as the dental polymerizable composition was charged into the same mold as mentioned above and was allowed to stand in a thermostat set at 37° C. for 30 minutes. Thus, the dental polymerizable composition was cured to obtain a test specimen.

The test specimen thus obtained was subjected to measurement of a lightness index L*W as measured against a white background and a lightness index L*B as measured against a black background using a spectrophotometric colorimeter (SE 2000, illuminant D65, manufactured by NIPPON DENSHOKU INDUSTRIES CO., LTD.). The difference ΔL between L*W and L*B was calculated by the following equation.

$$\Delta L = L^*W - L^*B$$

The results are shown in Tables 1 to 4.

When the composition is used as a mobile tooth fixing material or a denture liner, the ΔL of the cured product of the composition is preferably 70 or more and more preferably 80 or more. When the composition is used as a dental cement or a dental self-adhesive composite resin, the ΔL of the cured product of the composition is preferably 40 or more and 65 or less.

Test Example 7: Stain Resistance

The chromaticity (L*1, a*1, b*1) (chromaticity before stain resistance test) of each of the test specimens used in the surface gloss test was measured using a spectrophotometric colorimeter (SE 2000, illuminant D65, manufactured by NIPPON DENSHOKU INDUSTRIES CO., LTD.).

Next, the test specimen was immersed in an aqueous solution containing 1 mass % of dissolved instant coffee granules (Nescafe Gold Blend manufactured by Nestle Japan Ltd.) at 37° C. and allowed to stand in a thermostat set at 37° C. for 24 hours, after which the chromaticity (L*2, a*2, b*2) (chromaticity after stain resistance test) was measured again. The difference ΔE between the pre-staining chromaticity and the post-staining chromaticity was calculated by the following equation.

$$\Delta E = \{(L^*1-L^*2)^2+(a^*1-a^*2)^2+(b^*1-b^*2)^2\}^{1/2}$$

The results are shown in Table 1 to 4.

To achieve good color stability, ΔE needs to be 5 or less.

Test Example 8: Tensile Bond Strength

The labial surface of a bovine mandibular incisor was ground with #80 silicon carbide paper (manufactured by Nihon Kenshi Co., Ltd.) under running water, further ground with #1000 silicon carbide paper (manufactured by Nihon Kenshi Co., Ltd.), and then water on the surface was blown off with a dental air syringe. Thus, the bovine incisor having a flat enamel surface was obtained. A bovine incisor having a flat dentin surface was also obtained in the same manner.

An adhesive tape with a thickness of about 150 μm having a 3 mm-diameter circular hole was attached to the flat enamel surface of the bovine incisor thus obtained. Next, the dental polymerizable compositions for use as mobile tooth fixing materials prepared in Examples 1 to 6 and Comparative Examples 1 and 2 and the dental polymerizable compositions for use as dental self-adhesive composite resins prepared in Examples 21 to 24 and Comparative Examples 7 and 8 were each charged into the circular hole. An excess of the composition flowing out of the circular hole was removed with a razor blade to flatten the surface. The surface of the dental polymerizable composition charged was irradiated with light for 10 seconds using a dental visible light irradiation device (Pencure 2000 manufactured by Morita Corporation). A part of the surface of the dental polymerizable composition remained uncured. Next, a commercially available dental resin cement (PANAVIA 21 manufactured by Kuraray Noritake Dental Inc.) was applied to one end face of a stainless steel cylindrical rod (with a diameter of 7 mm and a length of 2.5 cm), and the rod was bonded to the surface of the dental polymerizable composition in such a manner that the one end face of the rod covered the surface of the composition. The resulting bovine incisor with the rod attached was allowed to stand at room temperature for 30 minutes, which was then immersed in distilled water and allowed to stand in a thermostat at 37° C. for 24 hours. Thus, five test samples (n=5) were obtained.

An adhesive tape with a thickness of about 150 μm having a 3 mm-diameter circular hole was attached to the flat dentin surface of the bovine incisor thus obtained. Next, the dental polymerizable compositions for use as dental self-adhesive composite resins prepared in Examples 19 to 24 and Comparative Examples 7 and 8 were each charged into the circular hole. An excess of the composition flowing out of the circular hole was removed with a razor blade to flatten the surface. The surface of the dental polymerizable composition charged was irradiated with light for 10 seconds using a dental visible light irradiation device (Pencure 2000 manufactured by Morita Corporation). A part of the surface of the dental polymerizable composition remained uncured. Next, a commercially available dental resin cement (PANAVIA 21 manufactured by Kuraray Noritake Dental Inc.) was applied to one end face of a stainless steel cylindrical rod (with a diameter of 7 mm and a length of 2.5 cm), and the rod was bonded to the surface of the dental polymerizable composition in such a manner that the one end face of the rod covered the surface of the composition. The resulting bovine incisor with the rod attached was allowed to stand at room temperature for 30 minutes, which was then immersed in distilled water and allowed to stand in a thermostat at 37° C. for 24 hours. Thus, five test samples (n=5) were obtained.

Each of the test samples (bovine incisors with stainless steel cylindrical rods attached) was connected to an Autograph tester (AG-100kNI manufactured by Shimadzu Corporation) to perform a tensile test at a crosshead speed of 2 mm/min. Thus, the bond strength between the dental polymerization composition and the flat enamel surface and that between the composition and the flat dentin surface were measured. The tensile test was carried out five times for each of these flat surfaces, and the average of the five measured values was determined as the tensile bond strength. The results are shown in Table 1 and Table 4.

When the tensile bond strength is 7.5 N or more, good adhesion is obtained.

Test Example 9: Polymerization Shrinkage Stress

The dental polymerizable compositions obtained in Examples 1 to 24 and Comparative Examples 1 to 8 were each charged into a ring-shaped mold (made of stainless steel and having an inner diameter of 5.5 mm and a thickness of 0.8 mm) placed on a glass plate (with a thickness of 4.0 mm) sandblasted with an aluminum powder having a particle diameter of 50 μm. A stainless steel jig (with a diameter of 5 mm) connected to an Autograph tester (AG-100kNI manufactured by Shimadzu Corporation) was placed on the dental polymerizable composition in the mold. The dental polymerizable compositions of Examples and Comparative Examples shown in Table 1 and Table 4 were each irradiated with light for 20 seconds through the glass plate using a dental visible light irradiation device (Pencure 2000 manufactured by Morita Corporation). The polymerization shrinkage stress that had occurred as the polymerization (curing) of the dental polymerizable composition proceeded by irradiation with light was measured using the Autograph tester. The results are shown in Table 1 and Table 4. The dental polymerizable compositions of Examples and Comparative Examples shown in Table 2 and Table 3 were each allowed to stand at 23° C. for 1 hour, during which the polymerization shrinkage stress that had occurred as the polymerization (curing) of the dental polymerizable composition proceeded was measured using the Autograph tester. The results are shown in Table 2 and Table 3.

The polymerization shrinkage stress is preferably 100 N or less and more preferably less than 85 N.

TABLE 1

| | | Ex. 1 | Ex. 2 | Ex. 3 | Ex. 4 | Ex. 5 | Ex. 6 | Com. Ex. 1 | Com. Ex. 2 |
|---|---|---|---|---|---|---|---|---|---|
| Raw materials | (Meth)acrylic block polymer (A)-1 | 100 | 20 | 200 | 100 | | | | |
| | (Meth)acrylic block polymer (A)-2 | | | | | 100 | | | |
| | (Meth)acrylic block polymer (A)-3 | | | | | | 100 | | |
| | (Meth)acrylic block polymer 1 | | | | | | | | 100 |
| | MDP (B)-1 | 20 | 20 | 20 | 30 | 20 | 20 | 20 | 20 |
| | 3G (B)-2 | 20 | 20 | 20 | 30 | 20 | 20 | 20 | 20 |
| | UDMA (B)-3 | 60 | 60 | 60 | 40 | 60 | 60 | 60 | 60 |
| | CQ (C-1)-1 | 0.4 | 0.3 | 0.5 | 0.4 | 0.4 | 0.4 | 0.4 | 0.4 |
| | BAPO (C-1)-2 | | | | 0.1 | | | | |
| | PDE (D)-1 | 0.6 | 0.45 | 0.75 | 0.6 | 0.6 | 0.6 | 0.6 | 0.6 |
| | Filler (E)-1 | 10 | 15 | 5 | 10 | 10 | 10 | 10 | 10 |
| | BHT | 0.01 | 0.01 | 0.01 | 0.01 | 0.01 | 0.01 | 0.01 | 0.01 |
| Properties | Discharging force (N) | 30 | 35 | 40 | 25 | 38 | 26 | 10 | 60 |
| | Formability: flow distance (mm) | 0 | 0.5 | 0 | 1.0 | 0 | 0 | 15 | 0 |
| | Flexural modulus (MPa) | 1000 | 1800 | 800 | 1200 | 1500 | 900 | 2800 | 1200 |
| | ΔL | 90 | 92 | 85 | 88 | 93 | 86 | 90 | 90 |
| | Stain resistance ΔE | 3.6 | 2.8 | 4.2 | 3.8 | 2.9 | 4.0 | 2.8 | 7.7 |
| | Tensile bond strength (bovine enamel) (MPa) | 12.5 | 11.5 | 12.2 | 13.8 | 11.8 | 12.0 | 5.8 | 10.5 |
| | Polymerization shrinkage stress (N) | 65 | 74 | 56 | 66 | 64 | 68 | 135 | 90 |

TABLE 2

| | | Ex. 7 | | Ex. 8 | | Ex. 9 | | Ex. 10 | | Ex. 11 | | Ex. 12 | | Com. Ex. 3 | | Com. Ex. 4 | |
|---|---|---|---|---|---|---|---|---|---|---|---|---|---|---|---|---|---|
| | | A | B | A | B | A | B | A | B | A | B | A | B | A | B | A | B |
| Raw materials | (Meth)acrylic block polymer (A)-1 | 200 | 200 | 100 | 100 | 400 | 400 | 200 | 200 | | | | | | | | |
| | (Meth)acrylic block polymer (A)-2 | | | | | | | | | 200 | 200 | | | | | | |
| | (Meth)acrylic block polymer (A)-3 | | | | | | | | | | | 200 | 200 | | | | |

TABLE 2-continued

|  |  | Ex. 7 | | Ex. 8 | | Ex. 9 | | Ex. 10 | | Ex. 11 | | Ex. 12 | | Com. Ex. 3 | | Com. Ex. 4 | |
| --- | --- | --- | --- | --- | --- | --- | --- | --- | --- | --- | --- | --- | --- | --- | --- | --- | --- |
|  |  | A | B | A | B | A | B | A | B | A | B | A | B | A | B | A | B |
|  | (Meth)acrylic block polymer 1 |  |  |  |  |  |  |  |  |  |  |  |  | 200 | 200 |  |  |
|  | UDMA (B)-3 | 10 | 10 | 10 | 10 | 10 | 10 | 20 | 20 | 10 | 10 | 10 | 10 | 10 | 10 | 10 | 10 |
|  | DFHM (B)-4 | 70 | 70 | 70 | 70 | 70 | 70 | 40 | 40 | 70 | 70 | 70 | 70 | 70 | 70 | 70 | 70 |
|  | BEM (B)-5 | 20 | 20 | 20 | 20 | 20 | 20 | 40 | 40 | 20 | 20 | 20 | 20 | 20 | 20 | 20 | 20 |
|  | THP (C-2)-1 | 2.0 |  | 1.0 |  | 3.0 |  |  |  | 2.0 |  | 2.0 |  | 2.0 |  | 2.0 |  |
|  | CHP (C-2)-2 |  |  |  |  |  |  | 2.0 |  |  |  |  |  |  |  |  |  |
|  | PTU (D)-2 |  | 2.0 |  | 1.0 |  | 3.0 |  |  |  |  |  | 2.0 |  | 2.0 |  | 2.0 |
|  | DMETU (D)-3 |  |  |  |  |  |  |  | 2.0 |  |  |  |  |  |  |  |  |
|  | VOAA (D)-4 |  | 0.01 |  | 0.01 |  | 0.02 |  |  |  |  |  | 0.01 |  | 0.01 |  | 0.01 |
|  | CUA (D)-5 |  |  |  |  |  |  |  | 0.001 |  |  |  |  |  |  |  |  |
|  | Filler (E)-1 | 5 | 5 | 10 | 10 |  |  | 5 | 5 | 5 | 5 | 5 | 5 | 5 | 5 | 5 | 5 |
|  | BHT | 0.01 | 0.01 | 0.01 | 0.01 | 0.01 | 0.01 | 0.01 | 0.01 | 0.01 | 0.01 | 0.01 | 0.01 | 0.01 | 0.01 | 0.01 | 0.01 |
| Properties | Discharging force (N) | 40 | | 35 | | 45 | | 40 | | 43 | | 36 | | 15 | | 65 | |
|  | Formability: flow distance (mm) | 0 | | 0 | | 0 | | 0 | | 0 | | 0 | | 11 | | 0 | |
|  | Type A hardness | 30 | | 40 | | 20 | | 28 | | 35 | | 26 | | 95 | | 40 | |
|  | Compression set (%) | 20 | | 25 | | 18 | | 22 | | 24 | | 24 | | fractured | | 43 | |
|  | ΔL | 90 | | 92 | | 85 | | 90 | | 92 | | 90 | | 92 | | 90 | |
|  | Stain resistance ΔE | 3.5 | | 2.9 | | 4.8 | | 3.7 | | 3.0 | | 4.0 | | 2.5 | | 7.2 | |
|  | Polymerization shrinkage stress (N) | 46 | | 52 | | 48 | | 44 | | 46 | | 55 | | 105 | | 85 | |

TABLE 3

|  |  | Ex. 13 | | Ex. 14 | | Ex. 15 | | Ex. 16 | | Ex. 17 | | Ex. 18 | | Com. Ex. 5 | | Com. Ex. 6 | |
| --- | --- | --- | --- | --- | --- | --- | --- | --- | --- | --- | --- | --- | --- | --- | --- | --- | --- |
|  |  | A | B | A | B | A | B | A | B | A | B | A | B | A | B | A | B |
| Raw materials | (Meth)acrylic block polymer (A)-1 | 100 | 100 | 50 | 50 | 200 | 200 | 100 | 100 |  |  |  |  |  |  |  |  |
|  | (Meth)acrylic block polymer (A)-2 |  |  |  |  |  |  |  |  | 100 | 100 |  |  |  |  |  |  |
|  | (Meth)acrylic block polymer (A)-3 |  |  |  |  |  |  |  |  |  |  | 100 | 100 |  |  |  |  |
|  | (Meth)acrylic block polymer 1 |  |  |  |  |  |  |  |  |  |  |  |  | 200 | 200 |  |  |
|  | 3G (B)-2 | 30 | 30 | 30 | 30 | 30 | 30 | 50 | 50 | 30 | 30 | 30 | 30 | 30 | 30 | 30 | 30 |
|  | D2.6E (B)-5 | 70 | 70 | 70 | 70 | 70 | 70 | 50 | 50 | 70 | 70 | 70 | 70 | 70 | 70 | 70 | 70 |
|  | THP (C-2)-1 | 2.0 |  | 1.0 |  | 3.0 |  |  |  | 2.0 |  | 2.0 |  | 2.0 |  | 2.0 |  |
|  | CHP (C-2)-2 |  |  |  |  |  |  | 2.0 |  |  |  |  |  |  |  |  |  |
|  | PTU (D)-2 |  | 2.0 |  | 1.0 |  | 3.0 |  |  |  | 2.0 |  | 2.0 |  | 2.0 |  | 2.0 |
|  | DMETU (D)-3 |  |  |  |  |  |  |  | 2.0 |  |  |  |  |  |  |  |  |
|  | VOAA (D)-4 |  | 0.01 |  | 0.01 |  | 0.02 |  |  |  | 0.01 |  | 0.01 |  | 0.01 |  | 0.01 |
|  | CUA (D)-5 |  |  |  |  |  |  |  | 0.001 |  |  |  |  |  |  |  |  |
|  | Filler (E)-2 | 0.5 | 0.5 | 1.0 | 1.0 |  |  | 0.5 | 0.5 | 0.5 | 0.5 | 0.5 | 0.5 | 0.5 | 0.5 | 0.5 | 0.5 |
|  | Filler (E)-3 | 200 | 200 | 300 | 300 | 100 | 100 | 200 | 200 | 200 | 200 | 200 | 200 | 200 | 200 | 200 | 200 |
|  | BHT | 0.01 | 0.01 | 0.01 | 0.01 | 0.01 | 0.01 | 0.01 | 0.01 | 0.01 | 0.01 | 0.01 | 0.01 | 0.01 | 0.01 | 0.01 | 0.01 |
| Properties | Discharging force (N) | 36 | | 35 | | 45 | | 40 | | 40 | | 35 | | 15 | | 72 | |
|  | Formability: flow distance (mm) | 0 | | 0 | | 0 | | 0 | | 0 | | 0 | | 8.4 | | 0 | |
|  | Flexural modulus (MPa) | 1500 | | 1900 | | 1000 | | 1600 | | 1800 | | 1200 | | 7300 | | 1800 | |
|  | ΔL | 52 | | 58 | | 43 | | 53 | | 55 | | 50 | | 64 | | 54 | |
|  | Stain resistance ΔE | 2.6 | | 2.2 | | 3.1 | | 2.8 | | 2.5 | | 3.2 | | 2.0 | | 8.1 | |
|  | Polymerization shrinkage stress (N) | 71 | | 78 | | 68 | | 69 | | 70 | | 72 | | 109 | | 93 | |

TABLE 4

|  |  | Ex. 19 | Ex. 20 | Ex. 21 | Ex. 22 | Ex. 23 | Ex. 24 | Com. Ex. 7 | Com. Ex. 8 |
| --- | --- | --- | --- | --- | --- | --- | --- | --- | --- |
| Raw materials | (Meth)acrylic block polymer (A)-1 | 100 | 20 | 200 | 100 |  |  |  |  |
|  | (Meth)acrylic block polymer (A)-2 |  |  |  |  | 100 |  |  |  |

TABLE 4-continued

| | | Ex. 19 | Ex. 20 | Ex. 21 | Ex. 22 | Ex. 23 | Ex. 24 | Com. Ex. 7 | Com. Ex. 8 |
|---|---|---|---|---|---|---|---|---|---|
| | (Meth)acrylic block polymer (A)-3 | | | | | | 100 | | |
| | (Meth)acrylic block polymer 1 | | | | | | | | 100 |
| | MDP (B)-1 | 20 | 20 | 20 | 30 | 20 | 20 | 20 | 20 |
| | 3G (B)-2 | 20 | 20 | 20 | 30 | 20 | 20 | 20 | 20 |
| | D2.6E (B)-5 | 60 | 60 | 60 | 40 | 60 | 60 | 60 | 60 |
| | CQ (C-1)-1 | 0.4 | 0.3 | 0.5 | 0.4 | 0.4 | 0.4 | 0.4 | 0.4 |
| | BAPO (C-1)-2 | | | | 0.1 | | | | |
| | PDE (D)-1 | 0.6 | 0.45 | 0.75 | 0.6 | 0.6 | 0.6 | 0.6 | 0.6 |
| | Filler (E)-2 | 1.0 | 1.5 | 0 | 1.0 | 1.0 | 1.0 | 1.0 | 1.0 |
| | Filler (E)-3 | 250 | 300 | 300 | 250 | 250 | 250 | 250 | 250 |
| | BHT | 0.01 | 0.01 | 0.01 | 0.01 | 0.01 | 0.01 | 0.01 | 0.01 |
| Properties | Discharging force (N) | 40 | 42 | 45 | 41 | 45 | 38 | 12 | 62 |
| | Formability: flow distance (mm) | 0 | 1.0 | 0 | 0.5 | 0 | 0 | 11 | 0 |
| | ΔL | 50 | 60 | 46 | 48 | 54 | 48 | 53 | 54 |
| | Stain resistance ΔE | 2.6 | 2.3 | 3.9 | 2.8 | 2.4 | 3.1 | 2.2 | 6.3 |
| | Tensile bond strength (bovine enamel) (MPa) | 10.0 | 9.5 | 8.8 | 9.8 | 9.9 | 9.6 | 3.9 | 8.4 |
| | Tensile bond strength (bovine dentin) (MPa) | 8.5 | 8.2 | 8.0 | 8.1 | 8.7 | 8.3 | 2.3 | 7.9 |
| | Polymerization shrinkage stress (N) | 75 | 83 | 70 | 78 | 78 | 72 | 136 | 85 |

As shown in Table 1, the dental polymerizable compositions of Examples 1 to 6 for use as mobile tooth fixing materials required a small discharging force but had a short flow distance, was easily formable, and had a low polymerization shrinkage stress during curing. The cured products of these compositions had a low flexural modulus, high surface gloss, high stain resistance, and high tensile bond strength to bovine enamel. In contrast, the dental polymerizable composition of Comparative Example 1 including no (meth)acrylic block copolymer was inferior in the formability, flexural modulus of the cured product, and tensile bond strength to bovine enamel and had a higher polymerization shrinkage stress. The dental polymerizable composition of Comparative Example 2 including no (meth)acrylic block copolymer (A) but including a (meth)acrylic block copolymer 1 having no curable functional group was inferior in the discharging force and stain resistance.

As shown in Table 2, the dental polymerizable compositions of Examples 7 to 12 for use as denture liners required a small discharging force but had a short flow distance, was easily formable, and had a low polymerization shrinkage stress during curing. The cured products of these compositions had a low type A hardness, a low compression set, high surface gloss, and high stain resistance. In contrast, the dental polymerizable composition of Comparative Example 3 including no (meth)acrylic block copolymer was inferior in the formability and had a high type A hardness when cured and a high polymerization shrinkage stress. In addition, this composition could not withstand a compression set test. The dental polymerizable composition of Comparative Example 4 including no (meth)acrylic block copolymer (A) but including a (meth)acrylic block copolymer 1 having no curable functional group required a large discharging force, and the cured product thereof had a high compression set and was inferior in stain resistance.

As shown in Table 3, the dental polymerizable compositions of Examples 13 to 18 for use as dental cements required a small discharging force but had a short flow distance, was easily formable, and had a low polymerization shrinkage stress during curing. The cured products of these compositions had a low flexural modulus, high surface gloss, and high stain resistance. In contrast, the dental polymerizable composition of Comparative Example 5 including no (meth)acrylic block copolymer was less formable and had a high polymerization shrinkage stress during curing, and the cured product thereof had a high flexural modulus. The dental polymerizable composition of Comparative Example 6 including no (meth)acrylic block copolymer (A) but including a (meth)acrylic block copolymer 1 having no curable functional group required a large discharging force, and the cured product thereof was inferior in stain resistance.

As shown in Table 4, the dental polymerizable compositions of Examples 19 to 24 for use as dental self-adhesive composite resins required a small discharging force but had a short flow distance, was easily formable, and had a low polymerization shrinkage stress during curing. The cured products of these compositions had high surface gloss and high stain resistance. These cured products also had high adhesion to tooth structure. In contrast, the dental polymerizable composition of Comparative Example 7 including no (meth)acrylic block copolymer was inferior in formability and tensile bond strength to bovine enamel and bovine dentin, and had a high polymerization shrinkage stress. The dental polymerizable composition of Comparative Example 8 including no (meth)acrylic block copolymer (A) but including a (meth)acrylic block copolymer 1 having no curable functional group required a large discharging force, and the cured product thereof was inferior in stain resistance.

INDUSTRIAL APPLICABILITY

The dental polymerizable composition of the present invention requires less discharging force, is easily formable, has lower polymerization shrinkage stress during curing, and exhibits higher stain resistance and surface gloss after being cured. The dental polymerizable composition of the present invention has good shock absorbing capacity and good adhesion to enamel when cured, in addition to the above properties, and thus is suitable for use as a mobile tooth fixing material or a dental cement. The dental polymerizable composition of the present invention further has high flexibility and distortion resistance when cured, in addition to the above properties, and thus is suitable for use as a denture liner. The dental polymerizable composition of the present invention has good adhesion to tooth structure (enamel and dentin), in addition to the above properties, and thus is suitable for use as a dental self-adhesive composite resin.

The invention claimed is:

1. A dental polymerizable composition, comprising:
   (A) a (meth)acrylic block copolymer (A) comprising a (meth)acrylic polymer block (a) having a curable functional group and a (meth)acrylic polymer block (b) having no curable functional group, the curable functional group having a partial structure of formula (1):

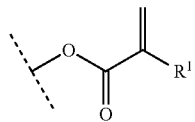

(1)

wherein $R^1$ is a hydrogen atom or a hydrocarbon group having 1 to 20 carbon atoms;
   (B) a polymerizable monomer (B) comprising a phosphoric acid group-containing polymerizable monomer; and
   (C) a polymerization initiator (C).

2. The dental polymerizable composition according to claim 1, wherein:
the curable functional group having the partial structure of formula (1) is a curable functional group of formula (2):

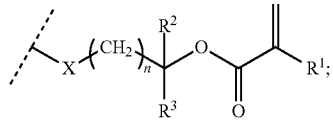

(2)

$R^1$ is a hydrogen atom or a hydrocarbon group having 1 to 20 carbon atoms;
$R^2$ and $R^3$ each independently is a hydrogen atom or a hydrocarbon group having 1 to 6 carbon atoms;
X is O, S, or $N(R^6)$;
$R^6$ is a hydrogen atom or a hydrocarbon group having 1 to 6 carbon atoms; and
n is an integer of 1 to 20.

3. The dental polymerizable composition according to claim 2, wherein:
$R^1$ is a hydrogen atom or a methyl group; and
X is O.

4. The dental polymerizable composition according to claim 1, further comprising:
   (D) a polymerization accelerator (D).

5. The dental polymerizable composition according to claim 1, further comprising:
   (E) a filler (E).

6. A mobile tooth fixing material, comprising the dental polymerizable composition according to claim 1.

7. A denture liner, comprising the dental polymerizable composition according to claim 1.

8. A dental cement, comprising the dental polymerizable composition according to claim 1.

9. A dental self-adhesive composite resin, comprising the dental polymerizable composition according to claim 1.

10. A dental polymerizable composition, comprising:
    (A) a (meth)acrylic block copolymer (A) comprising a (meth)acrylic polymer block (a) having a curable functional group and a acrylic polymer block (b) having no curable functional group, the curable functional group having a partial structure of formula (1):

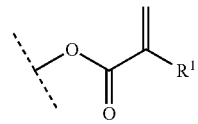

(1)

wherein $R^1$ is a hydrogen atom or a hydrocarbon group having 1 to 20 carbon atoms,
the acrylic polymer block (b) having no curable functional group is a polymer block consisting of a monomer unit formed by polymerizing a monomer containing an acrylic acid alkyl ester,
at least one (meth)acrylic polymer block (a) and at least one acrylic polymer block (b) are linked together;
    (B) a polymerizable monomer (B); and
    (C) a polymerization initiator (C).

11. The dental polymerizable composition according to claim 10, wherein:
the curable functional group having the partial structure of formula (1) is a curable functional group of formula (2):

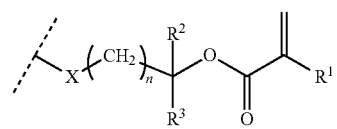

(2)

$R^1$ is a hydrogen atom or a hydrocarbon group having 1 to 20 carbon atoms;
$R^2$ and $R^3$ each independently is a hydrogen atom or a hydrocarbon group having 1 to 6 carbon atoms;
X is O, S, or $N(R^6)$;
$R^6$ is a hydrogen atom or a hydrocarbon group having 1 to 6 carbon atoms; and
n is an integer of 1 to 20.

12. The dental polymerizable composition according to claim 10, wherein:
$R^1$ is a hydrogen atom or a methyl group; and
X is O.

13. The dental polymerizable composition according to claim 10, further comprising:
    (D) a polymerization accelerator (D).

14. The dental polymerizable composition according to claim 10, further comprising:
    (E) a filler (E).

15. A denture liner, comprising the dental polymerizable composition according to claim 10.

16. A dental cement, comprising the dental polymerizable composition according to claim 10.

* * * * *